United States Patent [19]
Goble et al.

[11] Patent Number: 6,015,406
[45] Date of Patent: *Jan. 18, 2000

[54] ELECTROSURGICAL INSTRUMENT

[75] Inventors: Nigel Mark Goble; Colin Charles Owen Goble, both of Cardiff, United Kingdom

[73] Assignee: Gyrus Medical Limited, Cardiff, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/701,811

[22] Filed: Aug. 21, 1996

[30] Foreign Application Priority Data

Jan. 9, 1996 [GB] United Kingdom ............... 9600377
Jun. 20, 1996 [GB] United Kingdom ............... 9612996

[51] Int. Cl.$^7$ ................................... A61B 17/39
[52] U.S. Cl. ................. 606/41; 606/45; 606/46; 606/48; 606/50; 607/101
[58] Field of Search ............... 606/40–50; 607/99–104

[56] References Cited

U.S. PATENT DOCUMENTS

| Re. 33,925 | 5/1992 | Bales et al. . |
|---|---|---|
| 164,184 | 6/1875 | Kidder . |
| 1,366,756 | 1/1921 | Wappler . |
| 1,735,271 | 11/1929 | Groff . |
| 1,814,791 | 7/1931 | Ende . |
| 1,889,609 | 11/1932 | Mutscheller . |
| 1,932,258 | 10/1933 | Wappler . |
| 1,943,543 | 1/1934 | McFadden . |
| 1,952,617 | 3/1934 | Wappler . |
| 1,983,669 | 12/1934 | Kimble . |
| 2,050,904 | 8/1936 | Trice . |
| 2,056,377 | 10/1936 | Wappler . |
| 2,196,171 | 4/1940 | Arnesen . |
| 2,888,928 | 6/1959 | Seiger . |
| 3,035,580 | 5/1962 | Guiorguiev . |
| 3,460,539 | 8/1969 | Anhalt, Sr. . |
| 3,595,239 | 7/1971 | Petersen . |
| 3,601,126 | 8/1971 | Estes . |
| 3,614,414 | 10/1971 | Gores . |
| 3,648,001 | 3/1972 | Anderson et al. . |
| 3,685,518 | 8/1972 | Beurle et al. . |
| 3,699,967 | 10/1972 | Anderson . |

(List continued on next page.)

FOREIGN PATENT DOCUMENTS

| 0 013605 | 7/1980 | European Pat. Off. . |
|---|---|---|
| 0 049633 | 4/1982 | European Pat. Off. . |

(List continued on next page.)

OTHER PUBLICATIONS

Cook, Albert M. & John G. Webster, *Therapeutic Medical Devices Application and Design*, Prentice–Hall Inc., New Jersey, 1982, p. 349.

Pearce, John A., *Electrosurgery*, John Wiley & Sons Inc., New York, 1986, pp. 17, 69–75 and 87.

(List continued on next page.)

*Primary Examiner*—Jack W. Lavinder
*Assistant Examiner*—David M. Ruddy
*Attorney, Agent, or Firm*—Nixon & Vanderhye P.C.

[57] ABSTRACT

An electrosurgical instrument, which is used for the treatment of tissue in the presence of an electrically-conductive fluid medium, comprises an instrument shaft, and an electrode assembly at one end of the shaft. The electrode assembly comprises a tissue treatment electrode and a return electrode which is electrically insulated from the tissue treatment electrode by means of an insulation member. The tissue treatment electrode is exposed at the distal end portion of the instrument, and the return electrode has a fluid contact surface spaced proximally from the exposed end of the tissue treatment electrode by the insulation member. The exposed end of the tissue treatment electrode is constituted by a plurality of tissue treatment filamentary members made of an electrically-conductive material, the filamentary members being electrically connected to a common electrical supply conductor.

48 Claims, 6 Drawing Sheets

U.S. PATENT DOCUMENTS

| | | |
|---|---|---|
| 3,707,149 | 12/1972 | Hao et al. . |
| 3,801,766 | 4/1974 | Morrison, Jr. . |
| 3,815,604 | 6/1974 | O'Malley et al. . |
| 3,845,771 | 11/1974 | Vise . |
| 3,847,153 | 11/1974 | Weissman . |
| 3,885,569 | 5/1975 | Judson . |
| 3,898,991 | 8/1975 | Ikuno et al. . |
| 3,901,242 | 8/1975 | Storz . |
| 3,902,494 | 9/1975 | Haberlen et al. . |
| 3,903,891 | 9/1975 | Brayshaw . |
| 3,920,021 | 11/1975 | Hiltebrandt . |
| 3,920,022 | 11/1975 | Pastor . |
| 3,923,063 | 12/1975 | Andrews et al. . |
| 3,929,137 | 12/1975 | Gonser et al. . |
| 3,939,839 | 2/1976 | Curtiss . |
| 3,945,375 | 3/1976 | Banko . |
| 3,963,030 | 6/1976 | Newton . |
| 3,964,487 | 6/1976 | Judson . |
| 3,970,088 | 7/1976 | Morrison . |
| 3,974,833 | 8/1976 | Durden, III . |
| 4,011,872 | 3/1977 | Komiya . |
| 4,016,881 | 4/1977 | Rioux et al. . |
| 4,024,467 | 5/1977 | Andrews et al. . |
| 4,033,351 | 7/1977 | Hetzel . |
| 4,040,426 | 8/1977 | Morrison, Jr. . |
| 4,043,342 | 8/1977 | Morrison . |
| 4,051,855 | 10/1977 | Schneiderman . |
| 4,060,088 | 11/1977 | Morrison, Jr. et al. . |
| 4,069,827 | 1/1978 | Dominy . |
| 4,074,718 | 2/1978 | Morrison, Jr. . |
| 4,092,986 | 6/1978 | Schneiderman . |
| 4,114,623 | 9/1978 | Meinke et al. . |
| 4,116,198 | 9/1978 | Roos . |
| 4,119,102 | 10/1978 | LeVeen . |
| 4,126,137 | 11/1978 | Archibald . |
| 4,154,240 | 5/1979 | Ikuno et al. . |
| 4,189,685 | 2/1980 | Doss . |
| 4,200,104 | 4/1980 | Harris . |
| 4,202,337 | 5/1980 | Hren et al. . |
| 4,204,549 | 5/1980 | Paglione . |
| 4,210,152 | 7/1980 | Berry . |
| 4,228,800 | 10/1980 | Degler, Jr. et al. . |
| 4,248,231 | 2/1981 | Herczog et al. . |
| 4,271,837 | 6/1981 | Schuler . |
| 4,281,373 | 7/1981 | Mabille . |
| 4,301,802 | 11/1981 | Poler . |
| 4,326,529 | 4/1982 | Doss et al. . |
| 4,346,332 | 8/1982 | Walden . |
| 4,376,263 | 3/1983 | Pittroff et al. . |
| 4,381,007 | 4/1983 | Doss . |
| 4,416,277 | 11/1983 | Newton et al. . |
| 4,418,692 | 12/1983 | Guay . |
| 4,429,698 | 2/1984 | Bentall . |
| 4,448,198 | 5/1984 | Turner . |
| 4,474,179 | 10/1984 | Koch . |
| 4,476,862 | 10/1984 | Pao . |
| 4,492,231 | 1/1985 | Auth . |
| 4,494,541 | 1/1985 | Archibald . |
| 4,512,338 | 4/1985 | Balko et al. . |
| 4,517,976 | 5/1985 | Murakoshi et al. . |
| 4,524,770 | 6/1985 | Orandi . |
| 4,532,924 | 8/1985 | Auth et al. . |
| 4,534,347 | 8/1985 | Taylor . |
| 4,548,207 | 10/1985 | Reimels . |
| 4,559,943 | 12/1985 | Bowers . |
| 4,559,951 | 12/1985 | Dahl et al. . |
| 4,562,838 | 1/1986 | Walker . |
| 4,565,200 | 1/1986 | Cosman . |
| 4,567,890 | 2/1986 | Ohta et al. . |
| 4,580,557 | 4/1986 | Hertzmann . |
| 4,590,934 | 5/1986 | Malis et al. . |
| 4,593,691 | 6/1986 | Lindstrom et al. . |
| 4,617,927 | 10/1986 | Manes . |
| 4,657,015 | 4/1987 | Irnich . |
| 4,658,819 | 4/1987 | Harris et al. . |
| 4,658,820 | 4/1987 | Klicek . |
| 4,669,468 | 6/1987 | Cartmell et al. . |
| 4,674,499 | 6/1987 | Pao . |
| 4,681,122 | 7/1987 | Winters et al. . |
| 4,682,596 | 7/1987 | Bales et al. . |
| 4,688,569 | 8/1987 | Rabinowitz . |
| 4,696,668 | 9/1987 | Wilcox . |
| 4,706,667 | 11/1987 | Roos . |
| 4,709,698 | 12/1987 | Johnston et al. . |
| 4,712,544 | 12/1987 | Ensslin . |
| 4,727,874 | 3/1988 | Bowers et al. . |
| 4,735,201 | 4/1988 | O'Reilly . |
| 4,769,005 | 9/1988 | Ginsburg et al. . |
| 4,781,175 | 11/1988 | McGreevy et al. . |
| 4,799,480 | 1/1989 | Abraham et al. . |
| 4,800,899 | 1/1989 | Elliott . |
| 4,802,476 | 2/1989 | Noerenberg et al. . |
| 4,805,616 | 2/1989 | Pao . |
| 4,813,429 | 3/1989 | Eshel et al. . |
| 4,820,298 | 4/1989 | Leveen et al. . |
| 4,823,791 | 4/1989 | D'Amelio et al. . |
| 4,827,927 | 5/1989 | Newton . |
| 4,832,048 | 5/1989 | Cohen . |
| 4,850,353 | 7/1989 | Stasz et al. . |
| 4,860,744 | 8/1989 | Johnson et al. . |
| 4,878,493 | 11/1989 | Pasternak et al. . |
| 4,886,074 | 12/1989 | Bisping . |
| 4,919,129 | 4/1990 | Weber, Jr. et al. . |
| 4,920,978 | 5/1990 | Colvin . |
| 4,931,047 | 6/1990 | Broadwin et al. . |
| 4,936,281 | 6/1990 | Stasz . |
| 4,936,301 | 6/1990 | Rexroth et al. . |
| 4,936,310 | 6/1990 | Engstrom et al. . |
| 4,936,842 | 6/1990 | D'Amelio et al. . |
| 4,943,290 | 7/1990 | Rexroth et al. . |
| 4,950,267 | 8/1990 | Ishihara et al. . |
| 4,955,377 | 9/1990 | Lennox et al. . |
| 4,966,597 | 10/1990 | Cosman . |
| 4,967,765 | 11/1990 | Turner et al. . |
| 4,969,885 | 11/1990 | Farin . |
| 4,976,711 | 12/1990 | Parins et al. . |
| 4,994,069 | 2/1991 | Ritchart et al. . |
| 4,998,933 | 3/1991 | Eggers et al. . |
| 5,007,908 | 4/1991 | Rydell . |
| 5,009,656 | 4/1991 | Reimels ..................... 606/48 |
| 5,013,312 | 5/1991 | Parins et al. ............... 606/50 |
| 5,019,076 | 5/1991 | Yamanashi et al. . |
| 5,035,696 | 7/1991 | Rydell . |
| 5,037,379 | 8/1991 | Clayman et al. . |
| 5,047,026 | 9/1991 | Rydell . |
| 5,047,027 | 9/1991 | Rydell . |
| 5,057,107 | 10/1991 | Parins et al. . |
| 5,062,031 | 10/1991 | Flachenecker et al. . |
| 5,071,418 | 12/1991 | Rosenbaum . |
| 5,080,660 | 1/1992 | Buelna ..................... 606/50 |
| 5,083,565 | 1/1992 | Parins . |
| 5,085,659 | 2/1992 | Rydell . |
| 5,088,997 | 2/1992 | Delahuerga et al. . |
| 5,098,431 | 3/1992 | Rydell . |
| 5,099,840 | 3/1992 | Goble et al. . |
| 5,108,391 | 4/1992 | Flachenecker et al. . |
| 5,108,407 | 4/1992 | Geremia et al. . |
| 5,117,978 | 6/1992 | Blumenfeld et al. . |
| 5,122,138 | 6/1992 | Manwaring . |
| 5,133,365 | 7/1992 | Heil, Jr. et al. . |
| 5,158,561 | 10/1992 | Rydell et al. . |
| 5,167,658 | 12/1992 | Ensslin . |

| | | | | | | |
|---|---|---|---|---|---|---|
| 5,167,659 | 12/1992 | Ohtomo et al. . | | 5,472,441 | 12/1995 | Edwards et al. . |
| 5,171,255 | 12/1992 | Rydell . | | 5,472,443 | 12/1995 | Cordis et al. . |
| 5,171,311 | 12/1992 | Rydell et al. . | | 5,480,397 | 1/1996 | Eggers et al. . |
| 5,178,620 | 1/1993 | Eggers et al. . | | 5,480,398 | 1/1996 | Eggers et al. . |
| 5,190,517 | 3/1993 | Zieve et al. . | | 5,496,312 | 3/1996 | Klicek . |
| 5,195,959 | 3/1993 | Smith . | | 5,496,314 | 3/1996 | Eggers . |
| 5,196,007 | 3/1993 | Ellman et al. . | | 5,505,728 | 4/1996 | Ellman et al. . |
| 5,197,963 | 3/1993 | Parins . | | 5,505,730 | 4/1996 | Edwards et al. . |
| 5,201,743 | 4/1993 | Haber et al. . | | 5,507,743 | 4/1996 | Edwards et al. . |
| 5,207,675 | 5/1993 | Canady . | | 5,514,129 | 5/1996 | Smith . |
| 5,217,457 | 6/1993 | Delahuerga et al. . | | 5,514,130 | 5/1996 | Baker . |
| 5,217,458 | 6/1993 | Parins . | | 5,514,131 | 5/1996 | Edwards et al. . |
| 5,217,459 | 6/1993 | Kamerling . | | 5,520,684 | 5/1996 | Imran . |
| 5,221,281 | 6/1993 | Klicek ........................................ 606/45 | | 5,520,685 | 5/1996 | Wojciechowicz . |
| 5,244,462 | 9/1993 | Delahuerga . | | 5,522,815 | 6/1996 | Durgin, Jr. et al. . |
| 5,249,585 | 10/1993 | Turner et al. ............................. 607/99 | | 5,531,744 | 7/1996 | Nardella et al. . |
| 5,250,047 | 10/1993 | Rydell . | | 5,536,267 | 7/1996 | Edwards et al. . |
| 5,258,006 | 11/1993 | Rydell et al. . | | 5,540,680 | 7/1996 | Guglielmi et al. ........................ 606/41 |
| 5,259,395 | 11/1993 | Li . | | 5,540,681 | 7/1996 | Strul et al. . |
| 5,261,906 | 11/1993 | Pennino et al. . | | 5,540,682 | 7/1996 | Gardner et al. . |
| 5,267,994 | 12/1993 | Gentelia et al. . | | 5,540,683 | 7/1996 | Ichikawa et al. . |
| 5,267,997 | 12/1993 | Farin et al. . | | 5,540,684 | 7/1996 | Hassler, Jr. . |
| 5,277,201 | 1/1994 | Stern . | | 5,540,685 | 7/1996 | Parins et al. . |
| 5,277,696 | 1/1994 | Hagen . | | 5,542,916 | 8/1996 | Hirsch et al. . |
| 5,281,213 | 1/1994 | Milder et al. . | | 5,542,945 | 8/1996 | Fritz . |
| 5,281,216 | 1/1994 | Klicek . | | 5,545,161 | 8/1996 | Imran . |
| 5,282,799 | 2/1994 | Rydell . | | 5,545,193 | 8/1996 | Fleischman et al. . |
| 5,282,845 | 2/1994 | Bush et al. . | | 5,549,605 | 8/1996 | Hahnen . |
| 5,290,282 | 3/1994 | Casscells . | | 5,554,172 | 9/1996 | Horner et al. . |
| 5,290,283 | 3/1994 | Suda . | | 5,555,618 | 9/1996 | Winkler . |
| 5,300,068 | 4/1994 | Rosar et al. . | | 5,556,396 | 9/1996 | Cohen et al. . |
| 5,300,069 | 4/1994 | Hunsberger et al. . | | 5,556,397 | 9/1996 | Long et al. . |
| 5,300,070 | 4/1994 | Gentelia et al. . | | 5,558,671 | 9/1996 | Yates . |
| 5,304,214 | 4/1994 | DeFord et al. . | | 5,562,720 | 10/1996 | Stern et al. . |
| 5,306,238 | 4/1994 | Fleenor . | | 5,569,164 | 10/1996 | Lurz . |
| 5,318,563 | 6/1994 | Malis et al. . | | 5,569,242 | 10/1996 | Lax et al. . |
| 5,320,627 | 6/1994 | Sorensen et al. . | | 5,569,244 | 10/1996 | Hahnen . |
| 5,330,470 | 7/1994 | Hagen . | | 5,569,245 | 10/1996 | Guglielmi et al. . |
| 5,330,471 | 7/1994 | Eggers . | | 5,575,789 | 11/1996 | Bell et al. . |
| 5,334,193 | 8/1994 | Nardella . | | 5,578,007 | 11/1996 | Imran . |
| 5,334,198 | 8/1994 | Hart et al. . | | 5,582,609 | 12/1996 | Swanson et al. . |
| 5,336,222 | 8/1994 | Durgin, Jr. et al. . | | 5,582,610 | 12/1996 | Grossi et al. . |
| 5,342,357 | 8/1994 | Nardella . | | 5,584,830 | 12/1996 | Ladd et al. . |
| 5,342,391 | 8/1994 | Foshee et al. . | | 5,591,141 | 1/1997 | Nettekoven . |
| 5,344,428 | 9/1994 | Griffiths . | | 5,599,344 | 2/1997 | Paterson . |
| 5,352,222 | 10/1994 | Rydell . | | 5,599,345 | 2/1997 | Edwards et al. . |
| 5,354,296 | 10/1994 | Turkel ........................................ 606/49 | | 5,599,346 | 2/1997 | Edwards et al. . |
| 5,366,443 | 11/1994 | Eggers et al. . | | 5,599,347 | 2/1997 | Hart et al. . |
| 5,370,645 | 12/1994 | Klicek et al. . | | 5,599,348 | 2/1997 | Gentelia et al. . |
| 5,370,675 | 12/1994 | Edwards et al. . | | 5,599,349 | 2/1997 | D'Amelio . |
| 5,372,596 | 12/1994 | Klicek et al. . | | 5,603,711 | 2/1997 | Parins et al. . |
| 5,382,247 | 1/1995 | Cimino et al. . | | 5,603,712 | 2/1997 | Koranda et al. . |
| 5,383,874 | 1/1995 | Jackson et al. . | | 5,607,422 | 3/1997 | Smeets et al. . |
| 5,383,876 | 1/1995 | Nardella . | | 5,609,151 | 3/1997 | Mulier et al. . |
| 5,383,917 | 1/1995 | Desai et al. . | | 5,609,573 | 3/1997 | Sandock . |
| 5,383,923 | 1/1995 | Webster, Jr. . | | 5,611,798 | 3/1997 | Eggers . |
| 5,395,363 | 3/1995 | Billings et al. . | | 5,620,481 | 4/1997 | Desai et al. . |
| 5,395,368 | 3/1995 | Ellman et al. . | | 5,624,439 | 4/1997 | Edwards et al. . |
| 5,403,311 | 4/1995 | Abele et al. ............................. 606/48 | | 5,626,560 | 5/1997 | Soring . |
| 5,419,767 | 5/1995 | Eggers et al. . | | 5,626,575 | 5/1997 | Crenner . |
| 5,422,567 | 6/1995 | Matsunaga . | | 5,626,576 | 5/1997 | Janssen . |
| 5,423,808 | 6/1995 | Edwards et al. . | | 5,626,578 | 5/1997 | Tihon . |
| 5,423,809 | 6/1995 | Klicek . | | 5,628,745 | 5/1997 | Bek . |
| 5,423,810 | 6/1995 | Goble et al. . | | 5,628,771 | 5/1997 | Mizukawa et al. . |
| 5,423,811 | 6/1995 | Imran et al. . | | 5,630,426 | 5/1997 | Eggers et al. . |
| 5,431,649 | 7/1995 | Mulier et al. . | | 5,633,578 | 5/1997 | Eggers et al. . |
| 5,437,662 | 8/1995 | Nardella .................................. 606/48 | | 5,634,924 | 6/1997 | Turkel et al. . |
| 5,438,302 | 8/1995 | Goble . | | 5,672,174 | 9/1997 | Gough et al. ............................ 606/41 |
| 5,441,499 | 8/1995 | Fritzsch . | | 5,683,366 | 11/1997 | Eggers et al. . |
| 5,443,470 | 8/1995 | Stern et al. . | | 5,693,045 | 12/1997 | Eggers . |
| 5,454,809 | 10/1995 | Janssen . | | 5,697,281 | 12/1997 | Eggers et al. . |
| 5,462,521 | 10/1995 | Brucker et al. . | | 5,697,536 | 12/1997 | Eggers et al. . |

| | | | | | | |
|---|---|---|---|---|---|---|
| 5,697,882 | 12/1997 | Eggers et al. . | | 3622337 C2 | 1/1988 | Germany . |
| 5,697,909 | 12/1997 | Eggers et al. . | | 3642077 C2 | 6/1988 | Germany . |
| 5,700,262 | 12/1997 | Acosta et al. . | | 3708801 C2 | 9/1988 | Germany . |
| 5,766,153 | 6/1998 | Eggers et al. . | | 3824913 | 2/1990 | Germany . |
| 5,810,764 | 9/1998 | Eggers et al. . | | 3838840 C2 | 5/1990 | Germany . |
| 5,843,019 | 12/1998 | Eggers et al. . | | 3930451 | 3/1991 | Germany . |
| 5,860,951 | 1/1999 | Eggers et al. . | | 4108269 C2 | 6/1992 | Germany . |
| 5,871,469 | 2/1999 | Eggers et al. . | | 4103972 C2 | 8/1992 | Germany . |
| 5,873,855 | 2/1999 | Eggers et al. . | | 4126608 | 2/1993 | Germany . |
| 5,888,198 | 3/1999 | Eggers et al. . | | 4139029 C2 | 6/1993 | Germany . |
| 5,891,095 | 4/1999 | Eggers et al. . | | 4217999 A1 | 12/1993 | Germany . |

FOREIGN PATENT DOCUMENTS

| | | | | | | |
|---|---|---|---|---|---|---|
| | | | | 4237321 A1 | 5/1994 | Germany . |
| | | | | 4323585 | 1/1995 | Germany . |
| 0 067680 | 12/1982 | European Pat. Off. . | | 4339049 | 5/1995 | Germany . |
| 0 136855 | 4/1985 | European Pat. Off. . | | 4425015 | 1/1996 | Germany . |
| 0 219568 | 12/1985 | European Pat. Off. . | | 19530004A | 3/1996 | Germany . |
| 0 205851 | 12/1986 | European Pat. Off. . | | 4429478 | 3/1996 | Germany . |
| 0 280798A | 9/1988 | European Pat. Off. . | | 62-211060 | 9/1987 | Japan . |
| 0 310431 | 4/1989 | European Pat. Off. . | | 243478 | 7/1946 | Switzerland . |
| 0 316469 | 5/1989 | European Pat. Off. . | | 644491 | 1/1979 | U.S.S.R. . |
| 0 325456 | 7/1989 | European Pat. Off. . | | 1361497 | 7/1974 | United Kingdom . |
| 0 332308 | 9/1989 | European Pat. Off. . | | 2037167 | 7/1980 | United Kingdom . |
| 0 373670 | 6/1990 | European Pat. Off. . | | 1583397 | 1/1981 | United Kingdom . |
| 0 392837 | 10/1990 | European Pat. Off. . | | 2133290 | 7/1984 | United Kingdom . |
| 0 407057 | 1/1991 | European Pat. Off. . | | 2145932 | 4/1985 | United Kingdom . |
| 0 412426 | 2/1991 | European Pat. Off. . | | 2 161 081 | 7/1985 | United Kingdom . |
| 0 437377 | 7/1991 | European Pat. Off. . | | 2164473 | 3/1986 | United Kingdom . |
| 0 448798 | 10/1991 | European Pat. Off. . | | 2177309 | 1/1987 | United Kingdom . |
| 0 499491 | 8/1992 | European Pat. Off. . | | 2179861 | 3/1987 | United Kingdom . |
| 0 507622 | 10/1992 | European Pat. Off. . | | 2213381 | 8/1989 | United Kingdom . |
| 0 509 670 | 10/1992 | European Pat. Off. . | | 2214430 | 9/1989 | United Kingdom . |
| 0 517243 | 12/1992 | European Pat. Off. . | | WO 81/03271 | 11/1981 | WIPO . |
| 0 518230 | 12/1992 | European Pat. Off. . | | WO 82/00084 | 1/1982 | WIPO . |
| 0 530400 | 3/1993 | European Pat. Off. . | | WO 82/02488 | 8/1982 | WIPO . |
| 0 536440 | 4/1993 | European Pat. Off. . | | WO 84/03829 | 10/1984 | WIPO . |
| 0 558316 | 9/1993 | European Pat. Off. . | | WO 88/01851 | 3/1988 | WIPO . |
| 0 558318 | 9/1993 | European Pat. Off. . | | WO 90/03152 | 4/1990 | WIPO . |
| 0 647435 | 4/1995 | European Pat. Off. . | | WO 93/08756 | 5/1993 | WIPO . |
| 0 653192 | 5/1995 | European Pat. Off. . | | WO 93/13718 | 7/1993 | WIPO . |
| 0 667680 | 8/1995 | European Pat. Off. . | | WO 93/13816 | 7/1993 | WIPO . |
| 0 674909 | 10/1995 | European Pat. Off. . | | WO 93 16650 | 9/1993 | WIPO . |
| 0 684015 | 11/1995 | European Pat. Off. . | | WO 93/19681 | 10/1993 | WIPO . |
| 0 688536 | 12/1995 | European Pat. Off. . | | WO 93/19682 | 10/1993 | WIPO . |
| 0 692224 | 1/1996 | European Pat. Off. . | | WO 93/20747 | 10/1993 | WIPO . |
| 0 694290 | 1/1996 | European Pat. Off. . | | WO 93/20877 | 10/1993 | WIPO . |
| 0 697199 | 2/1996 | European Pat. Off. . | | WO 94/04220 | 3/1994 | WIPO . |
| 0 709065 | 5/1996 | European Pat. Off. . | | WO 94/06510 | 3/1994 | WIPO . |
| 0 714635 | 6/1996 | European Pat. Off. . | | WO 94/10921 | 5/1994 | WIPO . |
| 0 717967 | 6/1996 | European Pat. Off. . | | WO 94/10924 | 5/1994 | WIPO . |
| 0 754 437 | 1/1997 | European Pat. Off. . | | WO 94/10925 | 5/1994 | WIPO . |
| 57862 | 9/1953 | France . | | WO 94/23659 | 10/1994 | WIPO . |
| 1215305 | 4/1960 | France . | | WO 94/26228 | 11/1994 | WIPO . |
| 1454773 | 10/1966 | France . | | WO 94/28809 | 12/1994 | WIPO . |
| 2313949 | 1/1977 | France . | | WO 95/02369 | 1/1995 | WIPO . |
| 2443829 | 7/1980 | France . | | WO 95 05781 | 3/1995 | WIPO . |
| 2501034 | 9/1982 | France . | | WO 95/09576 | 4/1995 | WIPO . |
| 222207 | 5/1985 | German Dem. Rep. . | | WO 95/09577 | 4/1995 | WIPO . |
| 651428 | 9/1937 | Germany . | | WO 95/10320 | 4/1995 | WIPO . |
| 1007960 | 5/1957 | Germany . | | WO 95/10321 | 4/1995 | WIPO . |
| 2222820 | 11/1973 | Germany . | | WO 95/18575 | 7/1995 | WIPO . |
| 2457900 | 5/1976 | Germany . | | WO 95/19733 | 7/1995 | WIPO . |
| 2930982 | 2/1981 | Germany . | | WO 9517855 | 7/1995 | WIPO . |
| 3209444 | 10/1982 | Germany . | | WO 95/20360 | 8/1995 | WIPO . |
| 3215832A | 11/1982 | Germany . | | WO 95/23558 | 9/1995 | WIPO . |
| 3119735 | 1/1983 | Germany . | | WO 95/24160 | 9/1995 | WIPO . |
| 3245570 | 6/1984 | Germany . | | WO 95/25472 | 9/1995 | WIPO . |
| 3423356 | 1/1986 | Germany . | | WO 95/26686 | 10/1995 | WIPO . |
| 3427517 | 1/1986 | Germany . | | WO 95/30377 | 11/1995 | WIPO . |
| 3511107 | 10/1986 | Germany . | | WO 95/31144 | 11/1995 | WIPO . |
| 3623688 | 1/1987 | Germany . | | WO 96/00036 | 1/1996 | WIPO . |
| 3530335 | 3/1987 | Germany . | | WO 96/00039 | 1/1996 | WIPO . |
| 3707820 | 9/1987 | Germany . | | WO 96/00040 | 1/1996 | WIPO . |

| | | |
|---|---|---|
| WO 96/00042 | 1/1996 | WIPO . |
| WO 96/00043 | 1/1996 | WIPO . |
| WO 96/00528 | 1/1996 | WIPO . |
| WO 96/04859 | 2/1996 | WIPO . |
| WO 96/07360 | 3/1996 | WIPO . |
| WO 96/09010 | 3/1996 | WIPO . |
| WO 96/10367 | 4/1996 | WIPO . |
| WO 96/14020 | 5/1996 | WIPO . |
| WO 96/14021 | 5/1996 | WIPO . |
| WO 96/18349 | 6/1996 | WIPO . |
| WO 96/19152 | 6/1996 | WIPO . |
| WO 96/23448 | 8/1996 | WIPO . |
| WO 96/23449 | 8/1996 | WIPO . |
| WO 96/24296 | 8/1996 | WIPO . |
| WO 96/24301 | 8/1996 | WIPO . |

OTHER PUBLICATIONS

Wyeth, G.A., *Electrosurgical Unit,* pp. 1180–1202.

Everest Medical Technologies, Inc., "Everest Bipolar Laparoscopic Cholecystectomy," Transcript of Lecture by Dr. Olsen, Oct. 7, 1991.

Dobbie, A.K., "The Electrical Aspects of Surgical Diathermy," Biomedical Engineering, May 1969, pp. 206–216.

Valleylab, Excerpts from Valleylab SSE2L Instruction Manual, Valleylab Part No. A 945 110 005 H, Jan. 6, 1983.

Schurr, M. O. et al., "Histologic Effects of Different Technologies for Dissection in Endoscopic Surgery:ND:YAG Laser, High Frequency and Water–Jet," End. Surg., vol. 2, 1994, pp. 195–201.

Newman, Laura, "Could Twist on TURP Knock Lasers Out, "Urology times, vol. 3, Mar. 3, 1995, p. 21.

ArthroCare Corporation, "The Arthocare Arthroscopic System, "1995.

Tucker, R.D. et al., "In Vivo Effect of 5 French Bipolar and Monopolar Electro–Surgical Probes on Porcine Bladder," Urological Research, Springer–Verlag 1990, 18:291–294.

Kramolowsky, Eugene V. et al., "The Urological Application of Electrosurgery," The Journal of Urology vol. 146, Sept. 1991, pp. 669–674.

Tucker, Robert D. et al., "A Comparison of Urologic Application of Bipolar Versus Monopolar Five French Electrosurgical Probes, "The Journal of Urology, 141, Mar. 1989, pp. 662–665.

Kramolowsky, Eugene V. et al., "Use of 5F Bipolar Electrosurgical Probe in Endoscopic Urological Procedures," The Journal of Urology, vol. 143, Feb. 1990, pp. 275–277.

Tucker, Robert et al., "A Bipolar Electrosurgical TURP Loop " Abstract of Paper P14–11, 7th World Congress on Endourology and ESWL, Nov. 27–30, Kyoto, Japan, 1989, p. 248.

Ramsay, J.W. A. et al., "A Comparison of Bipolar and Monopolar Diathermy Probes in Experimental Animals," Urological Research, Springer–Verlag 1985, 13:99–102.

German Article w/ Translation:Elsasser, E. and Roos, E., "Concerning an Instrument for Transurethral Resection without Leakage of Current,"Medizinal–Marks/Acta Medicotechnica, vol. 24, No. 4, 1976, pp. 129–134.

Nardella, Paul C., "Radio Frequency Energy and Impedance Feedback," SPIE, vol. 1068, Catheter–Based Sensing & Imaging Technology, 1989, pp.42–48.

Honig, William M., "The Mechanism of Cutting in Electrosurgery," IEEE Transactions on Biomedical Engineering, Jan. 1975, pp. 58–65.

Barry, Kevin J. et al., "The Effect of Radiofrequency–Generated Thermal Energy on the Mechanical and Histologic Characteristics of the Arterial Wall In Vivo: Implications for Radiofrequency Angioplasty," American Heart Journal, vol. 117, No. 2, Feb. 1989, pp. 332–341.

Slager, Cornelis J. et al., "Vaporization of Atherosclerotic Plaques by Spark Erosion," Journal of American College of Cardiology, 1985, pp. 1382–1386.

Lee, Benjamin I. et al., "Thermal Compression and Molding of Artherosclerotic Vascular Tissue with Use of Radiofrequency Energy: Implications for Radiofrequency Balloon Angioplasty," *Journal of American College of Cardiology,* vol. 13, No. 5, Apr. 1989, pp. 1167–1175.

Piercey, J.R.A. et al., "Electrosurgical Treatment of Experimental Bleeding Canine Gastric Ulcers," Gastroenterology, vol. 74, No. 3, 1978, pp. 527–534.

Protell, Robert L. et al., "Computer–Assisted Electrocoagulation: Biopolar vs. Monopolar in the Treatment of Experimental Canine Gastric Ulcer Bleeding," Gastroenterology, vol. 80, No. 3, 1981, pp.451–455.

Johnston, James H. et al., "Experimental Comparison of Endoscopic Yttrium–Aluminum–Garnet Laser, Electrosurgery, and Heater Probe for Canine Gut Arterial Coagulation," Gastroenterology, vol. 92, No. 5, May 1987, pp. 1101–1108.

Dennis, M.B. et al., "Evaluation of Electrofulguration in Control of Bleeding of Experimental Gastric Ulcers," Digestive Diseases and Sciences, vol. 24, No. 11, Nov. 1979, pp. 845–848.

Silverstein, Fred E. et al., "Endoscopic Hemostasis Using Laser Photocoagulation and Electrocoagulation," Digestive Diseases and Sciences, vol. 26, No. 7, Jul. 1981 Supplement, pp. 31s–40s.

Auth, D.C., "Animal Testing of Endoscopic Hemostasis with Laser and Other Devices," Endoscopy, vol. 18, Supplement May 2, 1986, pp. 36–39.

McLean, A. J., "The Bovie Electrosurgical Current Generator –Some Underlying Principles and Results," Archives of Surgery, vol. 18, 1929, pp. 1863–1873.

McLean, A. J., "Characteristics of Adequate Electrosurgical Current," American Journal of Surgery, vol. XVIII, No. 3, Feb. 16, 1932, pp. 417–441.

Wattiez, Arnaud et al., *Electrosurgery in Operative Endoscopy,* Blackwell Science Ltd., London, 1995, pp. 87–93, 155–163.

Farin, G., "Pneumatically Controlled Bipolar Cutting Instrument," End. Surg., 1993, pp. 1–3.

Muller, W., "The Advantages of Laparoscopic Assisted Bipolar High–Frequency Surgery," End. Surg., 1993, pp. 1–6.

Reidenbach, H. D., "Fundamentals of Bipolar High–Frequency Surgery," End. Surg. 1993, pp. 85–90.

Penketh, Richard et al., "Clinical Evaluation of the Procision Bipolar Electrosurgical Generator During Laparoscopic Gynaecological Procedures," EAES, 2nd International Congress of the European Association for Endoscopic Surgery, Madrid, Sept. 15–17, 1994.

Lloyd, David M. et al., "A New Portable Bipolar Generator–Use in Laparoscopic Cholecystectomy," EAES, 2nd International Congress of the European Association for Endoscopic Surgery, Madrid, Sept. 15–17, 1994.

Buchelt, Martin et al., "Excimer Laser Ablation of Fibrocartilage: An In Vitro Study," Lasers in Surgery and Medicine, vol. 11, 1991, pp. 271–279.

Srinivasan, R., "Ablation of Polymers and Biological Tissue by Ultraviolet Lasers," Science, vol. 234, Oct. 31, 1986, pp. 559–565.

Pearce, John A., "Chapter 3 Electrosurgery," *Handbook of Biomedical Engineering,* Ed. Jacob Kline, Academic Press, Inc., 1988, pp. 99–113.

Selikowitz, Staurt M. et al., "Electric Current and Voltage Recording on the Myocardium During Electrosurgical Procedures in Canines," *Reprint from Surgery, Gynecology & Obstetrics,* Mar. 1987, vol. 164, pp. 219–224.

Tucker, Robert D. et al., "Demodulated Low Frequency Currents from Electrosurgical Procedures," Surgery, Gynecology & Obstetrics, Jul. 1984, vol. 159, pp. 39–43.

Lu, David Y. et al., "Electrical Thermal Angioplasty: Catheter Design Features, In Vitro Tissue Ablation Studies and In Vivo Experimental Findings," Am J Cardiol, vol. 60, 1987, pp. 1117–1122.

Malis, Leonard I., "Electrosurgery: Technical Note," vol. 85, 1996, pp. 970–975.

Geddes, Leslie A., *Medical Device Accidents —With Illustrative Cases,* CRC Press, New York, 1998, p. 93 (commentary on Honig, William M., "The Mechanism of Cutting in Electrosurgery," IEEE Transactions on Biomedical Engineering, Jan. 1975, pp. 58–65).

Slager, C. J. et al., "Spark Erosion of Arteriosclerotic Plaques," Kardiologie, vol. 76, Suppl. 6, 1987, pp. 67–71.

Valleylab, Inc., "Force Electrosurgical Generators Instruction Manual," Valleylab Part No. 945 110 039 A, Feb. 1987, pp. 59–62.

Valleylab, Inc., "Advances in Bipolar Electrosurgery for Laparoscopic Surgery," Advances in Bioplar Electrosurgery, pp. 1–4.

Description of Codman and Johnson & Johnson Mails CMC–III Bipolar System.

Pfizer/Valleylab Press Release "Valleylab Inc. Introduces The Procision Bipolar Electrosurgery System," Sept.15, 1994.

ArthroCare Corporation, "ArthroCare Arthoscopic Electrosurgery System, Model 970 Operator's Manual," Feb. 1996.

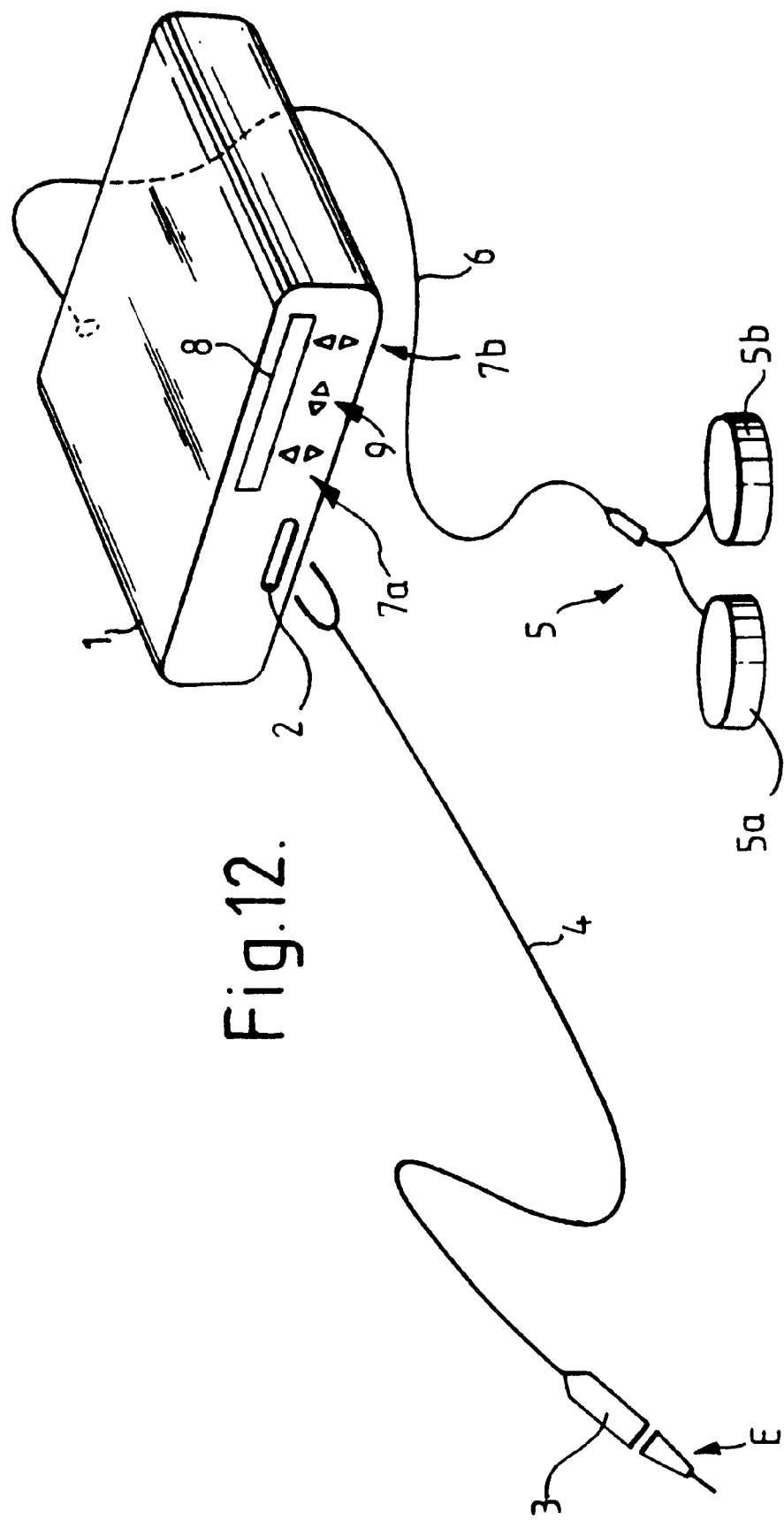

ELECTROSURGICAL INSTRUMENT

BACKGROUND OF THE INVENTION

This invention relates to an electrosurgical instrument for the treatment of tissue in the presence of an electrically conductive fluid medium, to electrosurgical apparatus including such an instrument, and to an electrode unit for use in such an instrument.

Endoscopic electrosurgery is useful for treating tissue in cavities of the body, and is normally performed in the presence of a distension medium. When the distension medium is a liquid, this is commonly referred to as underwater electrosurgery, this term denoting electrosurgery in which living tissue is treated using an electrosurgical instrument with a treatment electrode or electrodes immersed in liquid at the operation site. A gaseous medium is commonly employed when endoscopic surgery is performed in a distensible body cavity of larger potential volume in which a liquid medium would be unsuitable, as is often the case in laparoscopic or gastroenterological surgery.

Underwater surgery is commonly performed using endoscopic techniques, in which the endoscope itself may provide a conduit (commonly referred to as a working channel) for the passage of an electode. Alternatively, the endoscope may be specifically adapted (as in a resectoscope) to include means for mounting an electrode, or the electrode may be introduced into a body cavity via a separate access means at an angle with respect to the endoscope—a technique commonly referred to as triangulation. These variations in technique can be subdivided by surgical speciality, where one or other of the techniques has particular advantages given the access route to the specific body cavity. Endoscopes with integral working channels, or those characterised as resectoscopes, are generally employed when the body cavity may be accessed through a natural opening—such as the cervical canal to access the endometrial cavity of the uterus, or the urethra to access the prostate gland and the bladder. Endoscopes specifically designed for use in the endometrial cavity are referred to as hysteroscopes, and those designed for use in the urinary tract include cystoscopes, urethroscopes and resectoscopes. The procedures of transurethal resection or vaporisation of the prostate gland are known as TURP and EVAP respectively. When there is no natural body opening through which an endoscope may be passed, the technique of triangulation is commonly employed. Triangulation is commonly used during underwater endoscopic surgery on joint cavities such as the knee and the shoulder. The endoscope used in these procedures is commonly referred to as an arthroscope.

Electrosurgery is usually carried out using either a monopolar instrument or a bipolar instrument. With monopolar electrosurgery, an active electrode is used in the operating region, and a conductive return plate is secured to the patient's skin. With this arrangement, current passes from the active electrode through the patient's tissues to the external return plate. Since the patient represents a significant portion of the circuit, input power levels have to be high (typically 150 to 250 watts), to compensate for the resistive current limiting of the patient's tissues and, in the case of underwater electrosurgery, power losses due to the fluid medium which is rendered partially conductive by the presence of blood or other body fluids. Using high power with a monopolar arrangement is also hazardous, due to the tissue heating that occurs at the return plate, which can cause severe skin burns. There is also the risk of capacitive coupling between the instrument and patient tissues at the entry point into the body cavity.

With bipolar electrosurgery, a pair of electrodes (an active electrode and a return electrode) are used together at the tissue application site. This arrangement has advantages from the safety standpoint, due to the relative proximity of the two electrodes so that radio frequency currents are limited to the region between the electrodes. However, the depth of effect is directly related to the distance between the two electrodes; and, in applications requiring very small electrodes, the inter-electrode spacing becomes very small, thereby limiting tissue effect and output power. Spacing the electrodes further apart would often obscure vision of the application site, and would require a modification in surgical technique to ensure correct contact of both electrodes with tissue.

There are a number of variations to the basic design of the bipolar probe. For example, U.S. Pat. No. 4,706,667 describes one of the fundamentals of the design, namely that the ratio of the contact areas of the return electrode and of the active electrode is greater than 7:1 and smaller than 20:1 for cutting purposes. This range relates only to cutting electrode configurations. When a bipolar instrument is used for desiccation or coagulation, the ratio of the contact areas of the two electrodes may be reduced to approximately 1:1 to avoid differential electrical stresses occurring at the contact between the tissue and the electrodes.

The electrical junction between the return electrode and tissue can be supported by wetting of the tissue by a conductive solution such as normal saline. This ensures that the surgical effect is limited to the needle or active electrode, with the electric circuit between the two electrodes being completed by the tissue. One of the obvious limitations with the design is that the needle must be completely buried in the tissue to enable the return electrode to complete the circuit. Another problem is one of the orientation: even a relatively small change in application angle from the ideal perpendicular contact with respect to the tissue surface, will change the contact area ratio, so that a surgical effect can occur in the tissue in contact with the return electrode.

Cavity distension provides space for gaining access to the operation site, to improve visualisation, and to allow for manipulation of instruments. In low volume body cavities, particularly where it is desirable to distend the cavity under higher pressure, liquid rather than gas is more commonly used due to better optical characteristics, and because it washes blood away from the operative site.

Conventional underwater electrosurgery has been performed using a non-conductive liquid (such as 1.5% glycine) as an irrigant, or as a distension medium to eliminate electrical conduction losses. Glycine is used in isotonic concentrations to prevent osmotic changes in the blood when intra-vascular absorption occurs. In the course of an operation, veins may be severed, with resultant infusion of the liquid into the circulation, which could cause, among other things, a dilution of serum sodium which can lead to a condition known as water intoxication.

The applicants have found that it is possible to use a conductive liquid medium, such as normal saline, in underwater endoscopic electrosurgery in place of non-conductive, electrolyte-free solutions. Normal saline is the preferred distension medium in underwater endoscopic surgery when electrosurgery is not contemplated, or a non-electrical tissue effect such as laser treatment is being used. Although normal saline (0.9% w/v; 150 mmol/l) has an electrical conductivity somewhat greater than that of most body tissue, it has the advantage that displacement by absorption or extravasation from the operative site produces little physiological effect, and the so-called water intoxication effects of non-conductive, electrolyte-free solutions are avoided.

Carbon dioxide is the preferred gaseous distension medium, primarily because of its non-toxic nature and high water solubility.

In endoscopic procedures in which the distension medium is a gas, the applicants have found that it is possible to use an electrically-conductive gas (such as argon) in place of carbon dioxide. Argon is conductive when excited into a discharge state, and has been employed in both endoscopic and conventional monopolar electrosurgery as a method of increasing the distance between the tissue and the instrument, by providing a conductive path between the two when high voltage electrosurgical outputs such as spray or fulgurate are being used. The high voltages used in this application result in a very low penetration of the electrosurgical effect into the tissue, making the technique only suitable to control bleeding from multiple small blood vessels. This allows the surgeon to staunch bleeding from multiple sites in a surgical wound using a rapid "painting" technique, rather than applying electrosurgery to each individual bleeding site. The argon gas is delivered through a hollow surgical instrument, and passes over the monopolar electrode exposed at the tip of the instrument as a stream. This produces a region at the operative site which is rich in argon, and which contributes to the distension of the body cavity. High voltage monopolar electrosurgical outputs are undesirable in endoscopic surgery, because of the risks of damaging structures outside the field of vision, by either capacitive or direct coupling to a portion of the instrument remote from the operative site often outside the field of vision of the operator.

The applicants have developed a bipolar instrument suitable for underwater electrosurgery using a conductive liquid or gaseous medium. This electrosurgical instrument for the treatment of tissue in the presence of a fluid medium, comprises an instrument body having a handpiece and an instrument shaft and an electrode assembly, at one end of the shaft. The electrode assembly comprises a tissue treatment electrode which is exposed at the extreme distal end of the instrument, and a return electrode which is electrically insulated from the tissue treatment electrode and has a fluid contact surface spaced proximally from the exposed part of the tissue treatment electrode. In use of the instrument, the tissue treatment electrode is applied to the tissue to be treated whilst the return electrode, being spaced proximally from the exposed part of the tissue treatment electrode, is normally spaced from the tissue and serves to complete an electrosurgical current loop from the tissue treatment electrode through the tissue and the fluid medium. This electrosurgical instrument is described in the specification of the applicants' co-pending British Patent Application No. 9512889.8.

The electrode structure of this instrument, in combination with an electrically conductive fluid medium largely avoids the problems experienced with monopolar or bipolar electrosurgery. In particular, input power levels are much lower than those generally necessary with a monopolar arrangement (typically 100 watts). Moreover, because of the relatively large spacing between its electrodes, an improved depth of effect is obtained compared with conventional bipolar arrangement.

The aim of the invention is to provide an improved electrosurgical instrument of this type.

SUMMARY OF THE INVENTION

The present invention provides an electrosurgical instrument for the treatment of tissue in the presence of an electrically-conductive fluid medium, the instrument comprising an instrument shaft, and an electrode assembly at one end of the shaft, the electrode assembly comprising a tissue treatment electrode and a return electrode which is electrically insulated from the tissue treatment electrode by means of an insulation member, the tissue treatment electrode being exposed at the distal end portion of the instrument, and the return electrode having a fluid contact surface spaced proximally from the exposed end of the tissue treatment electrode by the insulation member, wherein the exposed end of the tissue treatment electrode is constituted by a plurality of tissue treatment filamentary members made of an electrically-conductive material, the filamentary members being electrically connected to a common electrical supply conductor.

The return electrode is spaced from the tissue treatment electrode so that, in use, it does not contact the tissue to be treated, and so that the electrical circuit is always completed by the conductive fluid, and not simply by arcing between the electrodes. Indeed, the arrangement is such that arcing between adjacent parts of the electrode assembly is avoided, thereby ensuring that the tissue treatment electrode can become enveloped in a vapour pocket so that tissue entering the vapour pocket becomes the preferred path for current to flow back to the return electrode via the conductive fluid.

The electrosurgical instrument of the invention is useful for dissection, resection, vaporisation, desiccation and coagulation of tissue and combinations of these functions with particular application in hysteroscopic surgical procedures. Hysteroscopic operative procedures may include: removal of submucosal fibroids, polyps and malignant neoplasms; resection of congenital uterine anomalys such as a septum or subseptum; division of synechiae (adhesiolysis); ablation of diseased or hypertrophic endometrial tissue; and haemostasis.

The instrument of the invention is also useful for dissection, resection, vaporisation, desiccation and coagulation of tissue and combinations of these functions with particular application in arthroscopic surgery as it pertains to endoscopic and percutaneous procedures performed on joints of the body including, but not limited to, such techniques as they apply to the spine and other non-synovial joints. Arthroscopic operative procedures may include: partial or complete meniscectomy of the knee joint including meniscal cystectomy; lateral retinacular release of the knee joint; removal of anterior and posterior cruciate ligaments or remnants thereof; labral tear resection; acromioplasty, bursectomy and subacromial decompression of the shoulder-joint; anterior release of the temperomandibularjoint; synovectomy, cartilage debridement, chondroplasty, division of intra-articular adhesions, fracture and tendon debridement as applied to any of the synovial joints of the body; inducing thermal shrinkage of joint capsules as a treatment for recurrent dislocation, subluxation or repetitive stress injury to any articulated joint of the body; discectomy either in the treatment of disc prolapse or as part of a spinal fusion via a posterior or anterior approach to the cervical, thoracic and lumbar spine or any other fibrous joint for similar purposes; excision of diseased tissue; and haemostasis.

The instrument of the invention is also useful for dissection, resection, vaporisation, desication and coagulation of tissue and combinations of these functions with particular application in urological endoscopic (urethroscopy, cystoscopy, ureteroscopy and nephroscopy) and percutaneous surgery. Urological procedures may include: electro-vaporisation of the prostate gland (EVAP) and other variants of the procedure commonly referred to as transurethral resection of the prostate (TURP) including, but not limited to, interstitial ablation of the prostate gland by a percutaneous or peruretral route whether performed for benign or malignant disease; transurethaal or percutaneous resection of urinary tract tumours as they may arise as primary or secondary neoplasms and further as they may arise anywhere in the urological tract from the calyces of the kidney to the external urethral meatus; division of strictures as they may arise at the pelviureteric junction (PUJ), ureter, ureteral orifice, bladder neck or urethra; correction of ureterocoele; shrinkage of bladder diverticular; cystoplasty procedures as they pertain to corrections of voiding dysfunction; thermally induced shrinkage of pelvic floor as a corrective treatment for bladder neck descent; excision of diseased tissue; and haemostasis.

Surgical procedures using the instrument of the invention include introducing the electrode assembly to the surgical site through an artificial conduit (a cannula), or through a natural conduit which may be in an anatomical body cavity or space or one created surgically. The cavity or space may be distended during the procedure using a fluid or may be naturally held open by anatomical structures. The surgical site may be bathed in a continuous flow of conductive fluid such as saline solution to fill and distend the cavity. The procedures may include simultaneous viewing of the site via an endoscope or using an indirect visualisation means.

The invention also provides an electrode unit for an electrosurgical instrument for the treatment of tissue in the presence of an electrically-conductive fluid medium, the electrode unit comprising a shaft having at one end means for connection to an instrument handpiece, and, mounted on the other end of the shaft, an electrode assembly comprising a tissue treatment electrode and a return electrode which is electrically insulated from the tissue treatment electrode by means of an insulation member, the tissue treatment electrode being exposed at the distal end portion of the instrument, and the return electrode having a fluid contact surface spaced proximally from the exposed end of the tissue treatment electrode by the insulation member, wherein the exposed end of the tissue treatment electrode is constituted by a plurality of tissue treatment filamentary members made of an electrically-conductive material, the filamentary members being electrically connected to a common electrical supply conductor.

The invention further provides electrosurgical apparatus comprising a radio frequency generator and an electrosurgical instrument for the treatment of tissue in the presence of an electrically-conductive fluid medium, the instrument comprising an instrument shaft, and an electrode assembly at one end of the shaft, the electrode assembly comprising a tissue treatment electrode and a return electrode which is electrically insulated from the tissue treatment electrode by means of an insulation member, the tissue treatment electrode being exposed at the distal end portion of the instrument, the return electrode having a fluid contact surface spaced proximally from the exposed end of the tissue treatment electrode by the insulation member, and the radio frequency generator having a bipolar output connected to the electrodes, wherein the exposed end of the tissue treatment electrode is constituted by a plurality of tissue treatment filamentary members made of an electrically-conductive material, the filamentary members being electrically connected to the radio frequency generator by a common electric supply conductor.

The invention further provides a method of operating an electrosurgical apparatus having at least a tissue desiccation mode and a tissue vaporisation mode, the apparatus having a radio frequency generator coupled to an electrode assembly for the treatment of tissue in the presence of an electrically-conductive fluid medium, the electrode assembly comprising a tissue treatment electrode and a return electrode which is electrically insulated from the tissue treatment electrode by means of an insulation member, the tissue treatment electrode being exposed at the distal end portion of the assembly, the return electrode having a fluid contact surface spaced proximally from the exposed end of the tissue treatment electrode by the insulation member, and the exposed end of the tissue treatment electrode being constituted by a plurality of tissue treatment filamentary members made of an electrically-conductive material the filamentary members being electrically connected to the radio frequency generator by a common electrical supply conductor, the method comprising the step of:

controlling the output power of the radio frequency generator to lie within a first output range for the tissue desiccation mode and to lie within a second range for the tissue vaporisation mode, the first output range being such that the power supplied to the electrode assembly maintains the conductive fluid adjacent to the tissue treatment electrode substantially at boiling point for tissue desiccation without creating a vapour pocket surrounding the tissue treatment electrode, and the second output range is such that the output power supplied to the electrode assembly for vaporisation of tissue is such as to maintain a vapour pocket surrounding the tissue treatment electrode.

The invention still further provides an electrosurgical tissue desiccation method comprising the steps of:

providing an electrosurgical apparatus comprising a radio frequency generator coupled to an electrode assembly comprising a tissue treatment electrode and a return electrode, the tissue treatment electrode being exposed at the distal end portion of the assembly and being constituted by a plurality of tissue treatment filamentary members made of an electrically-conductive material, the filamentary members being electrically connected to the radio frequency generator by a common electrical conductor;

introducing the electrode assembly into a selected operation site with the tissue treatment electrode contacting the tissue to be treated, and with the tissue and the electrode assembly immersed in a conductive liquid;

activating the generator; and controlling the radio frequency power supplied to the electrode assembly by the generator to maintain the conductive liquid adjacent to the tissue treatment electrode substantially at its boiling point without creating a vapour pocket surrounding the tissue treatment electrode.

The invention also provides an electrosurgical method comprising the steps of:

providing an electrosurgical apparatus comprising a radio frequency generator coupled to an electrode assembly comprising a tissue treatment electrode and a return electrode, the tissue treatment electrode being exposed at the distal end portion of the assembly and being constituted by a plurality of tissue treatment filamentary members made of an electrically-conductive material, the filamentary members being electrically connected to the radio frequency generator by a common electrical supply conductor;

introducing the electrode assembly into a selected operation site with the tissue treatment electrode adjacent to the tissue to be treated, and with the tissue and the tissue electrode assembly immersed in a conductive liquid;

activating the generator; and applying sufficient radio frequency power to the electrode assembly to vaporise the conductive liquid surrounding the tissue treatment electrode to maintain a vapour pocket surrounding the tissue treatment electrode.

The invention still further provides a method of desiccating tissue using a bipolar electrode assembly, the bipolar electrode assembly including an active electrode and a return electrode, the active electrode having a plurality of tissue treatment filamentary members, said filamentary members each having a tip and a proximal portion, the method comprising the steps of:

(a) introducing the electrode assembly into a selected operation site;

(b) surrounding the electrode assembly with a conductive fluid;

(c) applying sufficient radio frequency output power to the electrode assembly to raise the temperature of the conductive fluid adjacent to the active electrode without creating a vapour pocket surrounding the active electrode;

(d) contacting one or more filament tips of the active electrode to the tissue while maintaining the return electrode out of contact with the tissue.

The invention also provides a method of vaporising tissue using a bipolar electrode assembly, the bipolar electrode assembly including an active electrode and a return electrode, the active electrode having a plurality of tissue treatment filamentary members, said filamentary members each having a tip and a proximal portion, the method comprising the steps of:

(a) introducing the electrode assembly into a selected operation site;

(b) surrounding the electrode assembly with a conductive fluid;

(c) applying sufficient radio frequency output power to the electrode assembly to vaporise the conductive fluid adjacent to the active electrode to create a vapour pocket surrounding the active electrode;

(d) positioning one or more filament tips of the active electrode adjacent to the tissue with the vapour pocket in contact with the tissue while maintaining the return electrode out of contact with the tissue.

BRIEF DESCRIPTION OF THE DRAWINGS

The invention will now be described in greater detail, by way of example with reference to the drawings, in which:

FIGS. 4a to 4e are diagrammatic side elevations of the electrode assembly of a second form of electrode unit constructed in accordance with the invention;

FIG. 12 is a diagram showing an electrosurgical apparatus constructed in accordance with the invention.

DETAILED DESCRIPTION OF THE DRAWINGS

Figure 2:
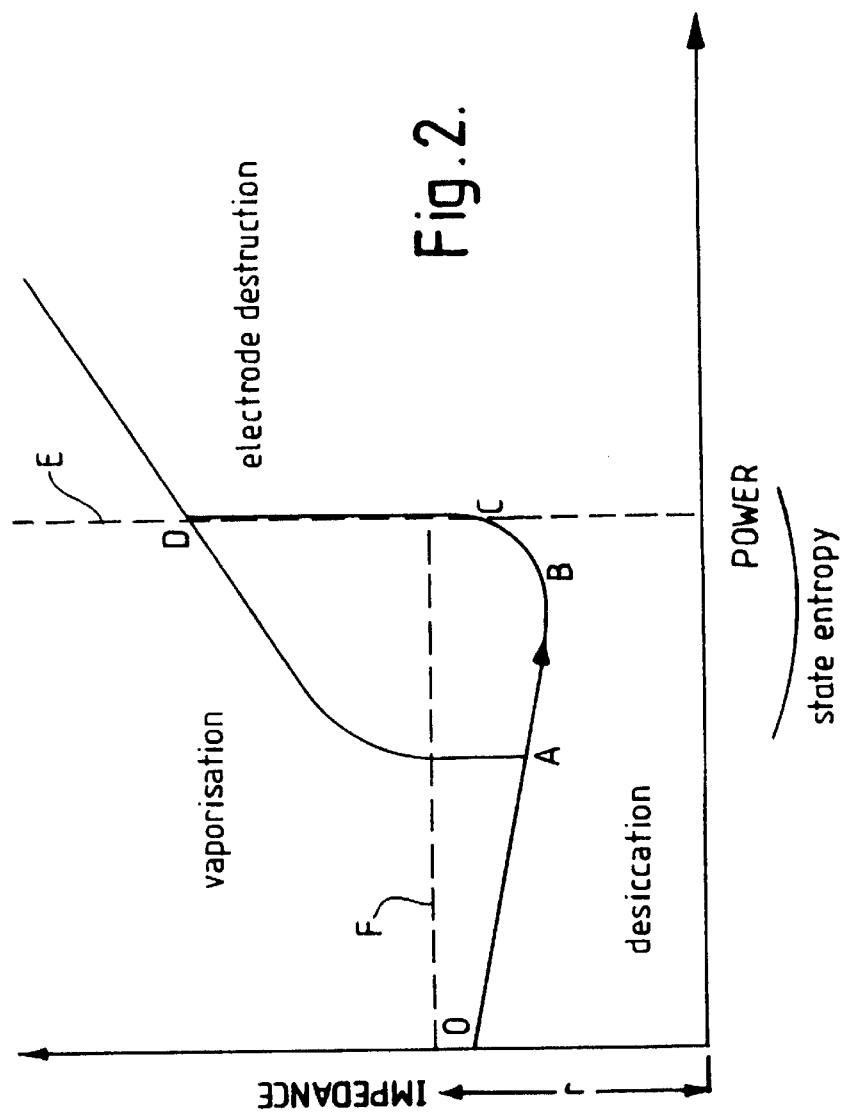
FIG. 2 is a graph illustrating the hysteresis which exists between the use of the electrode of FIG. 1 in desiccating and vaporising modes.

Each of the electrode units described below is intended to be used with a conductive distension medium such as normal saline, and each unit has a dual-electrode structure, with the conductive medium acting as a conductor between the tissue being treated and one of the electrodes, hereinafter called the return electrode. The other electrode is applied directly to the tissue, and is hereinafter called the tissue contact (active) electrode. In many cases, the use of a liquid distension medium is preferable, as it prevents excessive electrode temperatures in most circumstances, and largely eliminates tissue sticking.

Referring to the drawings, FIG. 12 shows electrosurgical apparatus including a generator 1 having an output socket 2 providing a radio frequency (RF) output for an instrument in the form of a handpiece 3 via a connection cord 4. Activation of the generator 1 may be performed from the handpiece 3 via a control connection in the cord 4, or by means of a footswitch unit 5, as shown, connected separately to the rear of the generator 1 by a footswitch connection cord 6. In the illustrated embodiment, the footswitch unit 5 has two footswitches 5a and 5b for selecting a desiccation mode and a vaporisation mode of the generator 1 respectively. The generator front panel has push buttons 7a and 7b for respectively setting desiccation and vaporisation power levels, which are indicated in a display 8. Push buttons 9a are provided as an alternative means for selection between the desiccation and vaporisation modes.

The handpiece 3 mounts a detachable electrode unit E, such as the electrode units E1 to E11 to be described below.

Figure 1:
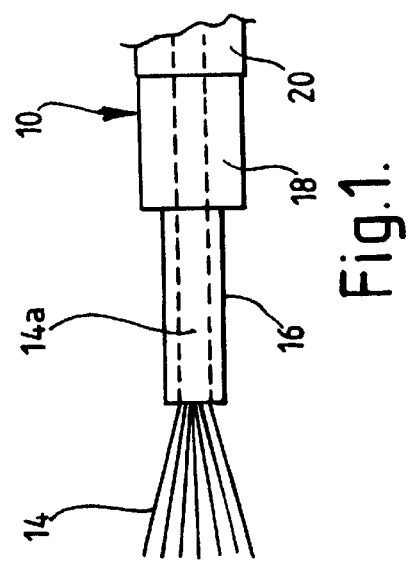
FIG. 1 is a diagrammatic side elevation of an electrode assembly at a distal end of a first form of electrode unit constructed in accordance with the invention.

FIG. 1 shows the first form of electrode unit E1 for detachable fastening to the electrosurgical instrument handpiece 3, the electrode unit comprising a shaft 10, which is constituted by a semi-flexible tube made of stainless steel or phynox electroplated in copper or gold, with an electrode assembly 12 at a distal end thereof. At the other end (not shown) of the shaft 10, means are provided for connecting the electrode unit E1 to a handpiece both mechanically and electrically.

The RF generator 1 (not shown in FIG. 1) delivers an electro-surgical current to the electrode assembly 12. The generator 1 includes means for varying the delivered output power to suit different electrosurgical requirements. The generator may be as described in the specification of our co-pending British Patent Application 9512888.0.

The electrode assembly 12 includes a central, tissue treatment (active) electrode 14 in the form of a brush electrode. The active electrode 14 is connected to the generator 1 via an integral central conductor 14a and a central copper conductor (not shown). The brush electrode 14 is constituted by a plurality of filaments of tungsten, the filaments having diameters lying in the range from 0.05 mm to 0.3 mm. A tapered ceramic insulation sleeve 16 surrounds the conductor 14a. A return electrode 18, which is constituted by the distal end portion of the shaft 10, abuts the proximal end of the sleeve 16. An outer insulating coating 20 surrounds the proximal portion of the shaft adjacent to the return electrode 18. The coating 20 would be polyvinylidene fluoride, a polyimide, polytetrafluoroethylene, a polyolefin, a polyester or ethylene tetrafluoroethylene.

By varying the output of the generator 1, the electrode unit E1 of FIG. 1 can be used for tissue removal by vaporisation, or for desiccation. FIG. 2 illustrates how the RF generator 1 can be controlled to take advantage of the hysteresis which exists between the desiccation and the vaporising modes of the electrode unit E1. Thus, assuming the electrode assembly 12 of the unit E1 is immersed in a conductive medium such as saline, there is an initial impedance "r" at point "O", the magnitude of which is defined by the geometry of the electrode assembly and the electrical conductivity of the fluid medium. The value of "r" will change when the active electrode 14 contacts tissue, the higher the value of "r" the greater the propensity of the electrode assembly 12 to enter the vaporisation mode. When RF power is applied to the electrode assembly 12 the fluid medium heats up. Assuming the fluid medium is normal saline (0.9% w/v), the temperature coefficient of the fluid medium is positive, so that the corresponding impedance coefficient is negative. Thus, as power is applied, the impedance initially falls and continues to fall with increasing power to point "B", at which point the saline in intimate contact with the electrode assembly 12 reaches boiling point. Small vapour bubbles form on the surface of the active electrode 14 and the impedance then starts to rise. After point "B", as power is increased further, the positive power coefficient of impedance is dominant, so that increasing power now brings about increasing impedance.

As a vapour pocket forms from the vapour bubbles, there is an increase in the power density at the residual electrode/ saline interface. There is, however, an exposed area of the active electrode 14 not covered by vapour bubbles, and this further stresses the interface, producing more vapour bubbles and thus even higher power density. This is a run-away condition, with an equilibrium point only occurring once the electrode is completely enveloped in vapour. For given set of variables, there is a power threshold before this new equilibrium can be reached (point "C").

The region of the graph between the points "B" and "C", therefore, represents the upper limit of the desiccation mode. Once in the vaporisation equilibrium state, the impedance rapidly increases to around 1000 ohms, with the absolute value depending on the system variables. The vapour pocket is then sustained by discharges across the vapour pocket between the active electrode 14 and the vapour/saline interface. The majority of power dissipation occurs within this pocket, with consequent heating of the active electrode 14. The amount of energy dissipation, and the size of the pocket, depends on the output voltage. If this is too low, the pocket will not be sustained, and if it is too high the electrode assembly 12 will be destroyed. Thus, in order to prevent destruction of the electrode assembly 12, the power output of the generator 1 must be reduced once the impedance has reached the point "D". It should be noted that, if the power is not reduced at this point, the power/impedance curve will continue to climb and electrode destruction would occur. The dotted line E indicates the power level above which electrode destruction is inevitable. As the power is reduced, the impedance falls until, at point "A", the vapour pocket collapses and the electrode assembly 12 reverts to the desiccation mode. At this point, power dissipation within the vapour pocket is insufficient to sustain it, so that direct contact between the active electrode 14 and the saline is re-established, and the impedance falls dramatically. The power density at the active electrode 14 also falls, so that the temperature of the saline falls below boiling point. The electrode assembly 12 is then in a stable desiccation mode. With the generator described in the specification of our co-pending British patent application 9604770.9, the output is 350 to 550 volts peak for the vaporisation mode, and about 170 volts peak for the desiccation mode.

It will be apparent that the electrode unit E1 of FIG. 1 can be used for desiccation by operating the unit in the region of the graph between the point "O" and a point in the region between the points "B" and "C". In this case, the electrode assembly 12 would be introduced into a selected operation site with the active electrode 14 adjacent to the tissue to be treated, and with the tissue, the active electrode and the return electrode 18 immersed in the saline. The RF generator 1 would then be activated (and cyclically controlled as described in the specification of our co-pending British patent application 9604770.9 to supply sufficient power to the electrode assembly 12 to maintain the saline adjacent to the active electrode 14 at, or just below, its boiling point without creating a vapour pocket surrounding the active tip. The electrode assembly would then be manipulated to cause heating and dessication of the tissue in a required region adjacent to the active electrode 14. The electrode unit E1 can be used for vaporisation in the region of the graph between the point "D" and the dotted line F which constitutes the level below which vaporisation cannot occur. The upper part of this curve is used for tissue removal by vaporisation. It should also be appreciated that the electrode unit E1 could be used for cutting tissue. In the cutting mode, the electrode unit E1 still operates with a vapour pocket, but this pocket is much smaller than that used for vaporisation, so that there is the least amount of tissue damage commensurate with cutting. Typically, the generator operates at about 270 volts peak for cutting.

The temperature generated at the active electrode 14 is of the order of 1500° C. in the vaporisation mode, so that the active electrode is made of a material that can withstand such high temperatures. Preferably, the active electrode 14 is made of tungsten, platinum or a platinum alloy (such as platinum/iridium or platinum/tungsten).

Figure 3A:
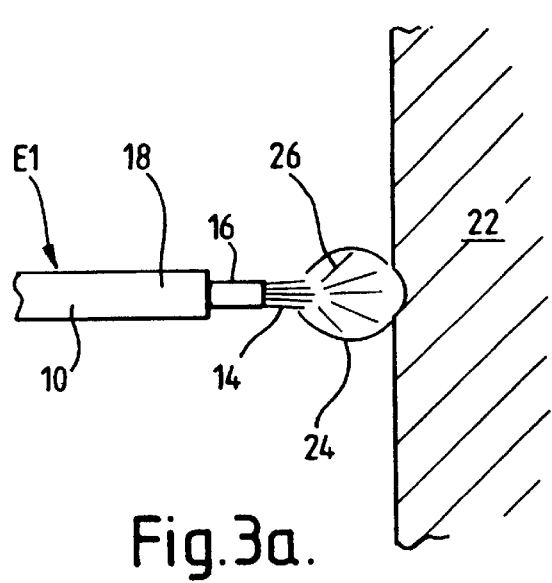
FIG. 3a is a diagrammatic side elevation of the first electrode unit, showing the use of such a unit for tissue removal by vaporisation.

FIG. 3a illustrates schematically the use of the electrode unit E1 of FIG. 1 for tissue removal by vaporisation. Thus, the electrode unit E1 creates a sufficiently high energy density at the active electrode 14 to vaporise tissue 22, and to create a vapour pocket 24 surrounding the active electrode. The formation of the vapour pocket 24 creates about a 10-fold increase in contact impedance, with a consequent increase in output voltage. Arcs 26 are created in the vapour pocket 24 to complete the circuit to the return electrode 18. Tissue 22 which contacts the vapour pocket 24 will represent a path of least electrical resistance to complete the circuit. The closer the tissue 22 comes to the active electrode 14, the more energy is concentrated to the tissue, to the extent that the cells explode as they are struck by the arcs 26, because the return path through the connective fluid (saline in this case) is blocked by the high impedance barrier of the vapour pocket 24. The saline solution also acts to dissolve the solid products of vaporisation.

Figure 3B:
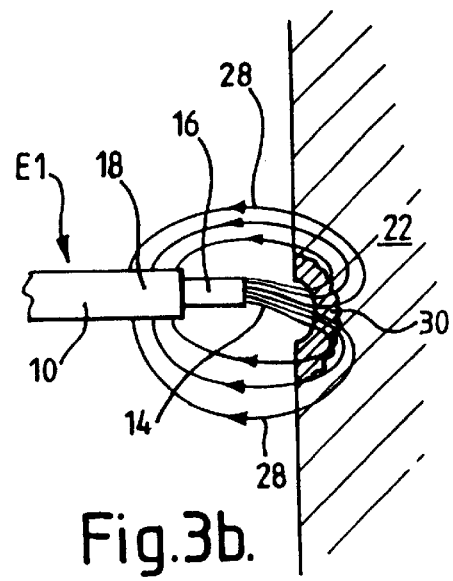
FIG. 3b is a diagrammatic side elevation of the first electrode unit, showing the use of such a unit, for tissue desiccation.

FIG. 3b illustrates schematically the use of the electrode unit E1 for tissue desiccation. In the desiccation mode, output power is delivered to the electrode assembly 12 in a first output range, so that current flows from the active electrode 14 to the return electrode 18. The output power causes the saline solution adjacent to the active electrode 14 to become heated, preferably to a point at or near the boiling point of the saline solution. This creates small vapour bubbles on the surface of the active electrode 14 that increase the impedance about the active electrode 14.

The body tissue 22 typically has lower impedance than the impedance of the combination of vapour bubbles and saline solution adjacent to the active electrode 14. When the active electrode 14 surrounded by small vapour bubbles and saline solution is brought into contact with the tissue 22, the tissue becomes part of the preferred electrical current path. Accordingly, the preferred current path goes out of the active electrode 14 at the point of tissue contact, through the tissue 22, and then back to the return electrode 18 via the saline solution, as shown by the current path lines 28 in FIG. 3b.

The invention has particular application in dessicating tissue. For tissue desiccation, one preferred approach is to contact only part of the active electrode 14 to the tissue 22, with the remainder of the active electrode remaining remote from the tissue and surrounded by saline solution, so that current can pass from the active electrode to its return electrode 18 via the saline solution, without passing through the tissue. For example, in the embodiment shown in FIG. 3b, only the distal portion of the active electrode 14 contacts the tissue 22, with the proximal portion remaining spaced away from the tissue.

The invention can achieve desiccation with no or minimal charring of the tissue 22. When the active electrode 14 contacts the tissue 22, current passes through the tissue, causing the tissue at, and around, the contact point to desiccate. The area and volume of desiccated tissue 30 expands generally radially outwardly from the point of contact. As the tissue 22 is desiccated, it loses its conductivity. As the area and volume of conductivity of the tissue is less than the conductivity of the heated saline solution surrounding the active electrode 14.

The current will prefer to follow the least impedance path. Accordingly, as the impedance of the tissue 22 increases (due to desiccation) to a point where it approaches or exceeds the impedance of the combination of vapour bubbles and saline solution surrounding the active electrode 14, the preferred electrical current path will shift to a new path through the vapour bubbles and saline solution. Accordingly, once a large enough portion of tissue is desiccated, most (or substantially all) the current flow necessarily shifts to pass directly from the active electrode 14 into the saline solution. Before the tissue 22 becomes charred or scorched, the increased impedance of the dissicated tissue so causes most of the current to follow the path through the saline solution. No current, or a very small amount of current, will continue to pass through the desiccated tissue, and charring will be prevented.

In the embodiment shown in FIG. 3b, the exposed, stranded portion of the active electrode 14 allows parts of the active electrode to contact the tissue surface, while still maintaining most of the active electrode exposed portion out of contact with the tissue. Because most of the exposed portion of the active electrode 14 is out of contact with the tissue 22, the current path will more easily shift, upon dessication of a sufficient tissue volume, from the path through the tissue to a path that goes directly from the active electrode to the saline solution.

When the electrode unit E1 is in the desiccation mode, the flexibility of the brush electrode 14 offers considerable advantages when working with small diameter electrodes in irregular body cavities in which large areas of tissue require desiccation. From a technical standpoint, the return:active ratio is variable from >1:1 in the "closed" form to <1:1 in the "splayed" form. This variability of the return:active ratio is explained in greater detail below with reference to FIGS. 4a to 4c.

Figures 4A, 4B, 4C:
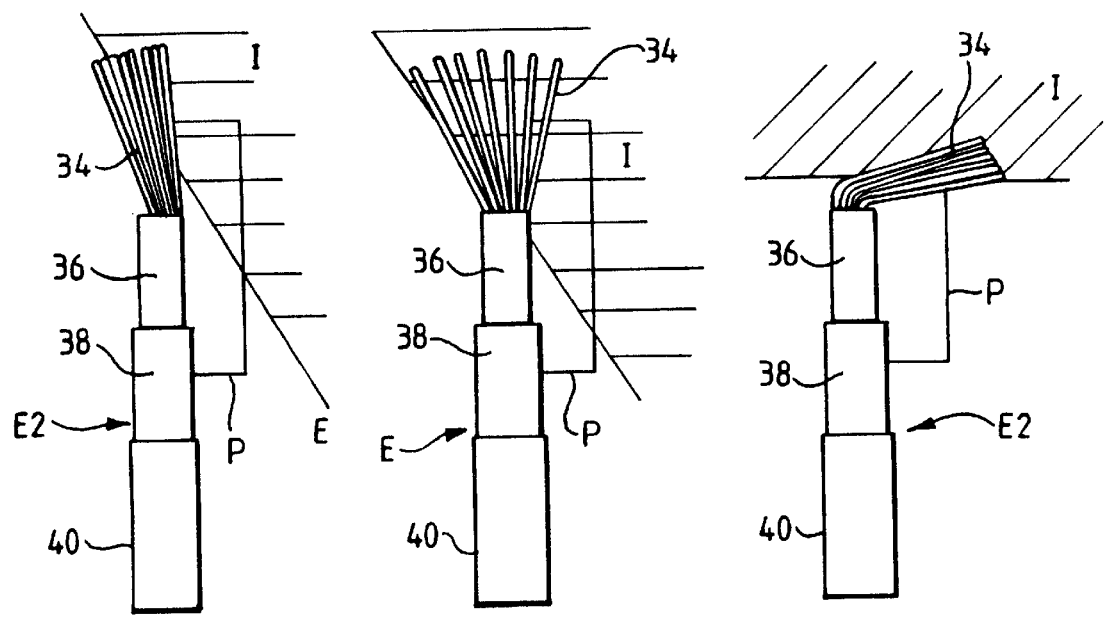

FIG. 4 shows the second form of electrode unit E2 whose electrode assembly 32 includes an active electrode 34 which is constituted by a plurality of filaments made of a conductive material such as stainless steel. The filaments of the brush electrode 34 are much longer (10 mm as compared with 5 mm) than the filaments of the brush electrode 14, as the electrode unit E2 is intended primarily for desiccation. In this embodiment, the return:active ratio is variable from >2:1 in the "closed" form to <1:1 in the "splayed" form. The electrode assembly 32 also includes a ceramic insulation sleeve 36, a return electrode 38 and an outer insulating sheath 40. The active electrode 34 is a brush electrode whose tip is flexible to provide a reproducible tissue effect which is substantially independent of the application angle of the electrode with respect to the surface of the tissue T (see FIG. 4c). Thus, the flexibility of the active electrode 34 results in differential contact areas of the active electrode dependent on the applied pressure. For example, FIG. 4a shows the brush electrode 34 "closed" during the application of light pressure, and FIG. 4b shows the brush "splayed" by firm tissue pressure. This enables the creation of a broader surgical effect than the diameter of the electrode 34 would otherwise allow, thereby reducing treatment time. FIGS. 4a to 4c also show the return path P for the current flow from the active electrode 34 to the return electrode 38 via the conductive medium.

This large variation in the return:active ratio is a feature which cannot be supported by conventional bipolar designs. This variation in ratio can occur because the conductive path to complete the electrical circuit is maintained by the low impedance of the electrode contact with the conductive fluid operating medium. In order to sustain the low impedance transfer of RF energy to the tissues, the RF generator must be controlled in such a way that vapour pockets cannot form at the interface between the active electrode and the tissue. This allows the tissue contact to be continually wetted by the conductive fluid so that, whilst the tissue water is removed by thermal desiccation, the impedance reaches an upper limit determined by a point just below a voltage threshold above which vapour pockets will start to form. This, combined with the greater insulation separation between the active and return electrodes, enables this type of electrode unit to deliver much higher powers effectively to the tissue for a given electrode dimension than any known electrode unit.

Figure 5A:
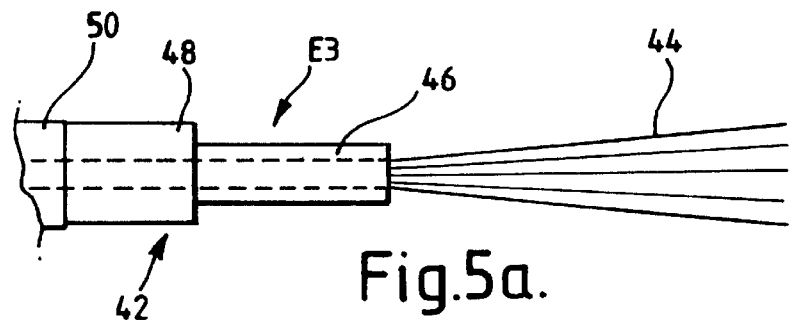
FIGS. 5a and 5b are diagrammatic side elevations of the electrode assembly of a third form of electrode unit constructed in accordance with the invention.
Figure 5B:
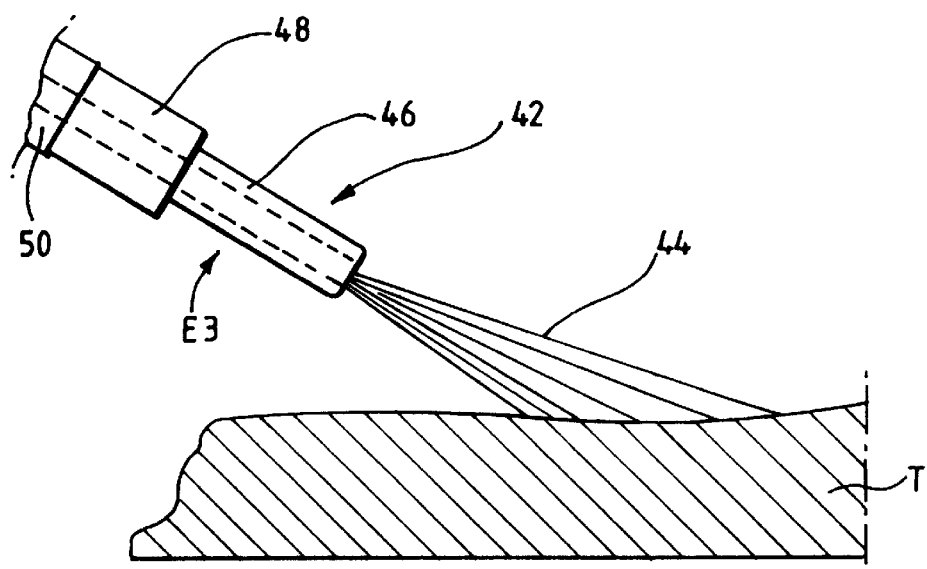

FIGS. 5a and 5b show the third form of electrode unit E3. This unit E3 is a modification of the electrode unit E2, and its electrode assembly 42 includes an active electrode 44 which is constituted by plurality of filaments made of stainless steel. The active electrode 44 is, therefore, a brush electrode and the filaments of this electrode are of a similar length to the filaments of the brush electrode 32. The electrode unit E3 is, therefore, intended primarily for desiccation. The electrode assembly 42 also includes a ceramic insulation sleeve 46, a return electrode 48 and an outer insulating sheath 50. The insulation sleeve 46 is made of a ceramic material and, like the insulation sleeve 16 of the electrode unit El, it tapers towards the distal end of the electrode assembly 42. FIG. 5a shows the electrode unit E3 in a non-operational position, and FIG. 5b shows the unit in desiccating mode against tissue T.

Figures 6A, 6B:
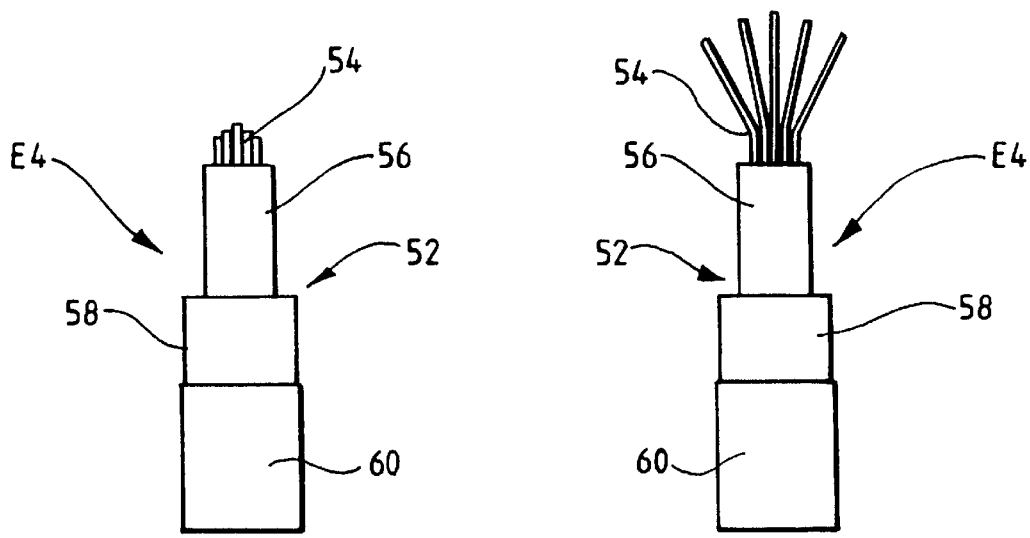
FIGS. 6a and 6b are diagrammatic side elevations of the electrode assembly of a fourth form of electrode unit constructed in accordance with the inventions.

FIGS. 6a and 6b show a fourth form of electrode unit E4 whose electrode assembly 52 includes an extensible active electrode 54 in the form of a brush electrode. The filaments of the brush electrode 54 are made of tungsten, platinum, platinum/tungsten or platinum/iridium. The electrode unit E4 also includes a ceramic insulation sleeve 56, a return electrode 58, and an insulating sheath 70. As shown in FIG. 6a, the active electrode 54 can be withdrawn substantially within the insulation sleeve 56 so that only the free end portions of its filaments are exposed. With the active electrode 54 in this position, the electrode unit E4 can be used to vaporise tissue in the manner described above with reference to FIG. 3. On the other hand, if the active electrode 54 is extended (see FIG. 6b), so that its filaments extend fully from the distal end of the sleeve 56, the electrode unit E4 can be used for desiccation. The ratio of the contact areas of the return to active electrodes of the unit E4 can, therefore, be varied between the fully retracted active electrode position (in which the ratio is high and the unit is used for vaporisation), and the extended position (in which the ratio is low and the unit is used for desiccation). The unit E4 achieves its dual functionality by varying the extent by which the filaments of the active electrode 54 are extended. Dual functionality could also be achieved by varying axial separation between the active electrode 54 and the return electrode 58 (for example by varying the length of the insulation sleeve 56). With a large extension of the filaments of the active electrode 54 or with a large axial electrode separation, a large electric field is created, so that more tissue is affected. With no extension of the filaments of the active electrode 54 or with a reduced electrode separation, a smaller electric field is produced, and is used for cutting or vaporisation in circumstances where no collateral thermal damage to tissue is desirable. The larger electric field pattern is desirable for desiccation, or in circumstances where the desiccation of collateral tissue is desirable to prevent haemorrhage from a cut surface.

Depending upon the ratio of the return:active electrode area, therefore, the brush electrode of the invention can have a dessication function (as exemplified by the embodiments of FIGS. 4 and 5), a vaporisation function (as exemplified by the embodiment of FIG. 3), or a dual desiccation/vaporisation function (as exemplified by the embodiment of FIG. 6).

As indicated above, the primary use for the desiccating brush is in providing a flexible, broad area electrode for desiccating large irregular areas of tissue. The requirement to treat such areas occurs in hysteroscopic surgery—desiccation of the endometrial lining of the uterus, and in urological surgery—desiccation and shrinkage of bladder diverticular. In both instances, the electrode is introduced through the working channel of the endoscope.

Introduction of the desiccating brush with a long and flexible, filamentous structure can prove problematical when the working channel of the endoscope is angled or includes steps in the inner bore. This can deform the brush filaments which, once inserted, cannot be adjusted and may not conform to the area of tissue to be treated. Bending back of the filaments may also inadvertently create an electrical short to the return electrode.

Figure 7A:
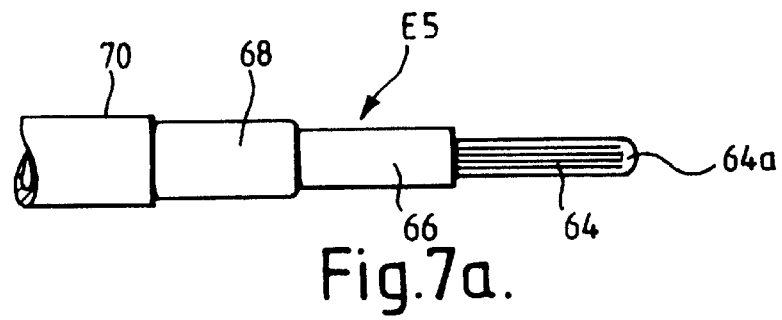
FIGS. 7a and 7b as diagrammatic side elevations of a fifth form of electrode unit constructed in accordance with the invention.
Figure 7B:
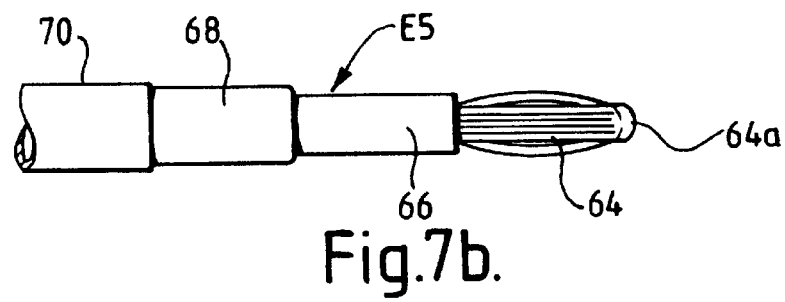

Whilst preserving the desired functions of flexibility and contact area geometry dependent on the pressure of application, the basic desiccating brush can be modified to overcome this problem. For example, the brush filaments can be simply twisted together. Preferably, however, the filaments are welded together at their distal ends as shown in FIG. 7 which shows a fifth form of electrode unit E5. The electrode unit E5 includes an active electrode 64 in the form of a brush electrode whose filaments are made of platinum, platinum/tungsten or platinumliridium. The distal ends 64a of the filaments are welded together as shown in FIG. 7a. This prevents distortion of the filaments in the working channel of an endoscope, whilst permitting bowing of the filaments (as shown in FIG. 7b) to increase tissue contact area. The electrode unit E5 includes a ceramic insulation sleeve 66, a return electrode 68 and an outer insulating sleeve 70.

In the dual function brush electrode, the return:active electrode area can be elevated to a level which is capable of producing tissue vaporisation. Obviously, with a very small active electrode area at the extreme of this range, the amount of tissue which can be desiccated becomes too small to be practically useful. If, however, the ratio is configured in the mid-range, then the same electrode can be used to produce both effective desiccation and tissue removal by vaporisation. The short brush described in FIG. 1 is one example of such a dual purpose electrode. Given that the filaments cannot be fabricated in stainless steel to support vaporisation, tungsten filaments are the preferred material in the short brush due to their rigidity overcoming the issues of distortion during introduction. Platinum alloys withstand the high vaporisation temperatures better than tungsten but, due to their flexibility and the annealing process during use, cannot be used in the short brush form. Platinum alloy dualfunction brush-type electrodes, therefore, require the modifications of twisting, braiding, or welding of the distal tips to prevent distortion.

These combined multi-functional brush electrode forms are particularly useful in removing tumour masses or polyps encountered during hysteroscopic and urological surgery. They can vaporise the tumour bulk, incise the stalks of polyps, and desiccate any bleeding vessels or the base of the tumour without the need to change electrodes.

In these multi-functional forms, the active electrode area is maximised for desiccation whilst still being capable of vaporisation or cutting functions. The minimum ratio depends on four important critera, namely:
1. The intrinsic impedance of the target tissue.
2. The volume of the body cavity.
3. The configuration of the active electrode.
4. The maximum output power from the RF generator.

The configuration of the active electrode obviously influences the ratio, with cylindrical forms representing the lowest ratio for a given length, but the other factors relate to the inability of the electrode to retain a vapour bubble. The filaments of the brush-type electrodes retain vapour bubbles, which helps maintain the vaporisation condition.

An arthroscope electrode may be characterised as short (100–140 mm), rigid with a working diameter up to 4 mm. It can be introduced through a stab incision into a joint cavity (with or without a cannula) using the triangulation technique. When an arthroscope includes a brush electrode of the type described above, it is operated with a motion which commonly moves the brush electrode between the 9 o'clock and 3 o'clock positions on the arthroscopic image.

As a result, the tissue to be treated is commonly approached at a shallow working angle with respect to the axis of the electrode. The electrode for arthoscopy thus needs to have an effect consistent with this angled approach to the tissue. The tissue to be treated, such as meniscal cartilage, is commonly dense and of a high electrical impedance, such tissue having a free edge representing a common injury site where treatment is required. Arthroscope electrodes are used where the joint spaces are commonly small (the joint spaces in the knee being typically 60–100 mls under fluid distension), so that, if vapour bubbles generated during vaporisation are large, problems with visualisation would occur.

Figure 8:
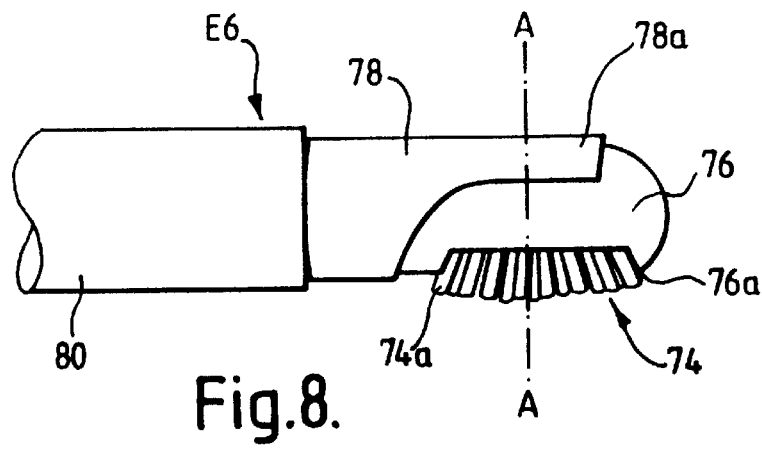
FIG. 8 is a diagrammatic side elevation of a sixth form of electrode unit constructed in accordance with the invention.

FIG. 8 shows an arthroscope electrode unit E6 constructed in accordance with the invention. The electrode unit E6 includes an active electrode 74 which is constituted by a plurality of filaments made of tungsten or an alloy of tungsten or platinum. The active (brush) electrode 74 is connected to an RF generator (not shown) via a central copper conductor (also not shown). A ceramic insulation sleeve 76 surrounds the central conductor, the filaments 74a of the brush electrode passing along the insulation sleeve and extending laterally therefrom through a cut-out 76a. A return electrode 78, which is constituted by the distal end of the instrument shaft, surrounds the proximal end of the sleeve 76. An outer insulating coating 80 (which would be polyvinylidene fluoride, a polyimide, polytetrafluoroethylene, a polyolefin, a polyester or ethylene tetrafluoroethylene) surrounds the proximal portion of the shaft adjacent to the return electrode 78. The return electrode 78 is formed with a hood-like extension 78a which extends over the surface of the sleeve 76 which is opposite to the cut-out 76a. The electrode unit E6 can, thus, provide maximum tissue engagement for shallow working angle applications, and is known as a side-effect electrode.

Because of the higher impedance of the target tissue, the arthroscopic multi-function brush electrode should support a lower ratio than electrodes designed for hysteroscopic and urological applications where the tissue is more vascular. Reducing the ratio does, however, have one drawback in body cavities of small volume, such as the knee joint which is typically 60–80 mls, and that is heating of the surrounded irrigant or distension fluid. Heating occurs primarily during the application of power to reach the vaporisation threshold. Once the threshold has been reached, the power requirement typically falls by 30–50%. Reducing the electrode ratio increases the power requirement to reach the threshold so that, despite the high impedance of the target tissue, it is undesirable to reduce the ratio to the lowest value capable of supporting vaporisation.

In addition, the high impedance is due to lack of vascularity of such tissues as meniscal cartilage. Except, therefore, when muscle or synovial tissue is being treated, the primary function of the athroscopic brush electrode is that it should provide rapid debulking of dense, avascular tissue. Desiccate functionality is not a requirement of such an instrument. Indeed, very short rigid brush electrodes with electrode ratios greater than 5:1 are desirable. The only reason for not elevating the ratio further is the need to engage the maximum amount of tissue and simultaneously reduce procedure time.

A short, rigid brush electrode (of the type described above with reference to FIG. 1 or FIG. 6a) can be thought of as an end-effect electrode which has tissue debulking precision with minimal thermal spread. Consequently, it can be used to create discrete holes in tissue, thereby to create an access channel to tissue deep to the surface, as may be required as part of an interstitial ablation technique on a tissue mass such as a prostate adenoma or a uterine fibroid (myolysis). This use of a vaporising, end effect, technique enables only the fibroid to be removed by complete debulking leaving a resection margin conforming to the "false capsule" of the fibroid. No normal tissue is removed and, due to control of collateral thermal effects at the endometrial resection margin, the scarring is reduced to a minimum, thereby increasing what chances there were of restoring fertility. Additionally, of course, vaporisation does not produce resection chippings to interfere with visualisation and prolong the procedure through the need to wash them out once the resection is completed. Conventional loop electrode resectoscopes require removal of normal tissue surrounding such fibroids, and this is disadvantageous because it increases the chance of bleeding, the risk of uterine perforation and the scarring of the uterus. This latter aspect is particularly undesirable when the procedure is being performed in an attempt to restore fertility.

Alternatively, a short, rigid brush electrode can be used to debulk a tumour (such as a fibroid, a bladder tumour or a prostate adenoma), or it can be used with the multiple puncture or drilling technique. In this case, after removing the intrauterine portion, the intramural portion can be treated by creating ("drilling") a series of holes into the abnormal tissue whether, for example, this is a fibroid or prostatic adenoma. To assess the depth of penetration, marks may be provided on the electrode shaft at measured distances from the tip, and hence to compare the depth of penetration against the pre-operative results of tests performed to establish size of the tumour or adenoma. The residual tissue bridges will shrink as part of the healing process. Whilst not removing the whole tumour, this technique is safer and quicker than removing the entire fibroid or prostatic adenoma, when treatment is being performed either for menorrhagia or bladder outflow obstruction, respectively.

Figure 9:
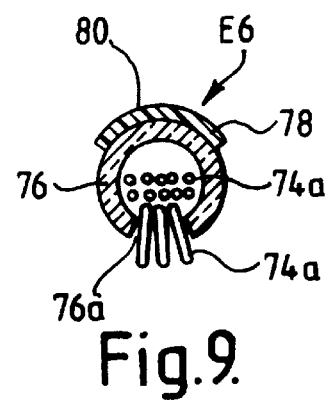
FIG. 9 is a cross-section taken on the line A—A of FIG. 8.

Another problem with working in the confined space of a joint cavity is in preventing damage to adjacent structures, particularly when the vaporising effect is enhanced, and both the tissue density and application angle make engagement and location difficult. This protection feature is intrinsic in the side-effect brush of FIG. 8, when the insulation sleeve 76 protects tissue above, below and behind the active electrode window 76a which only occupies a small arc of the cross-sectional form (as shown in FIG. 9).

Figure 10:
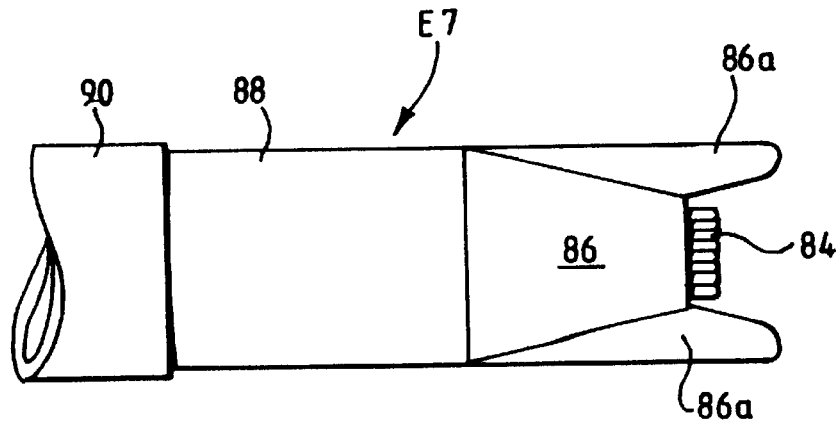
FIG. 10 is a diagrammatic side elevations of a seventh form of electrode unit constructed in accordance with the invention.

FIG. 10 shows the electrode assembly of the seventh form of electrode unit E7. This electrode assembly includes a central, tissue contact (active) electrode constituted by a plurality of filaments made of tungsten or an alloy of tungsten or platinum, a tapered ceramic insulation sleeve 86, a return electrode 88, and an outer insulating sleeve 90. The insulation sleeve 86 is formed with a pair of diametrically-opposed, forwardly-extending wings 86a which project beyond the active electrode 84 (0.5 mm in length). The filaments constituting the active electrode 86 extend only a short distance from the distal end of the insulation sleeve 86, thereby constituting a very short brush electrode. The electrode unit E7 has, therefore, a large return:active electrode ratio, so that this electrode unit is intended primarily for a tissue removal by vaporisation. The electrode unit E7 is particularly useful for electrosurgical operations on meniscal cartilage or any other elongate laminate structure which is to be treated from the side, as the wings 86a can be used to trap the cartilage against the active electrode 84. The configuration of the wings 86a also assists in preventing unnecessary exposure of the active electrode 84, which may otherwise damage adjacent structures when working in the confined spaces commonly encountered in endoscopic surgery.

Figure 11A:
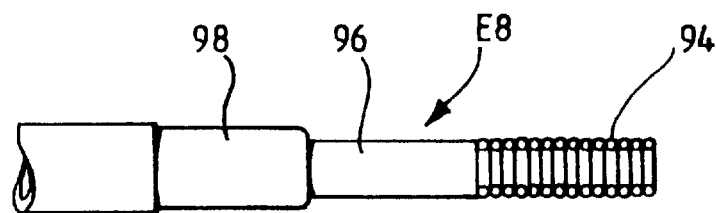
FIGS. 11a to 11d are diagrammatic side elevations of further forms of electrode unit constructed in accordance with the invention.
Figure 11B:
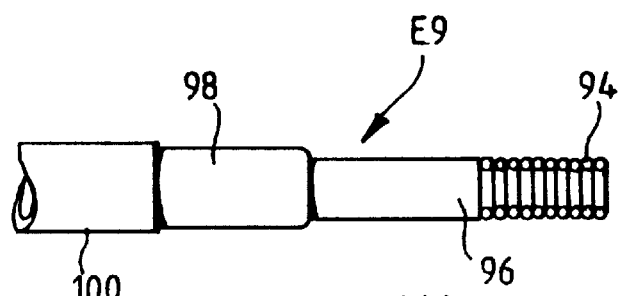
Figure 11C:
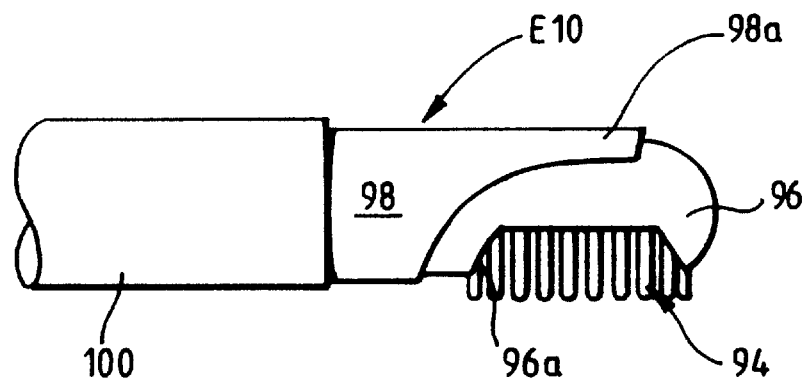
Figure 11D:
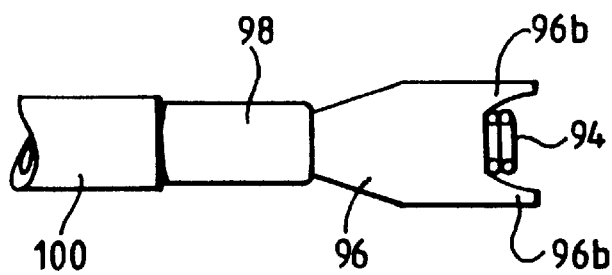

FIGS. 11a to 11d show eighth, ninth, tenth and eleventh forms of electrode unit E8 to E11, each of which incorporates an active electrode in the form of a coiled spring filament 94. The electrode units E8 to E11 each includes an insulation sleeve 96, a return electrode 98 and an insulating sheath 100. The electrode unit E8 of FIG. 11a is similar to that of FIG. 5a, being intended primarily for desiccation; and the electrode unit E9 of FIG. 11b is similar to that of FIG. 1, being intended primarily for vaporisation. The electrode unit E10 of FIG. 11c is similar to that of FIGS. 8 and 9, in that the coil electrode 94 is formed in a cut-out 96a formed the side of the insulation sleeve 96, and the return electrode 98 is formed with a hood-like extension 98a which extends over the surface of the sleeve 96 which is opposite to the cut-out 96a. The electrode unit E10 can, thus, provide maximum tissue engagement for shallow working angle applications, and is another form of side-effect electrode. The electrode unit E11 of FIG. 11d is similar to that of FIG. 10, in that the insulation sleeve 96 is formed with a pair of diametrically-opposed, forvardly-extending wings 96b. In each of these embodiments, the active electrode 94 is made of an alloy of platinum.

The electrode units E8 to E11 are similar to the brush-type electrodes of FIGS. 1 to 10, and have similar surgical effects, apart from the fact that they eliminate the risk of splaying (which is advantageous in certain electro-surgical procedures). They have, however, the advantage of simplifying the assembly procedure, particularly when using platinum alloy materials It will be apparent that modification could be made to the electrosurgical instruments described above. For example, the insulation sleeves 16, 36, 46, 56, 66, 76, 86 and 96 could be made of a silicone rubber (such as a silicone polyurethane), glass, a polymide, or a thermoplastics material.

We claim:

1. An electrosurgical instrument for the treatment of tissue in the presence of an electrically-conductive fluid medium, the instrument comprising:
   an instrument shaft, and an electrode assembly at one end of the shaft;
   the electrode assembly comprising a tissue treatment electrode and a return electrode which is electrically insulated from the tissue treatment electrode by means of an insulation member;
   the tissue treatment electrode being exposed at the distal end portion of the instrument, and the return electrode having an exposed fluid contact surface spaced proximally from the exposed end of the tissue treatment electrode by the insulation member to an extent that the return electrode remains out of contact with tissue undergoing treatment by the tissue treatment electrode, so that electrical current flow between the tissue and the return electrode occurs only on a path through the conductive fluid medium;
   the exposed end of the tissue treatment electrode is constituted by a plurality of tissue treatment filamentary members made of an electrically-conductive material, the filamentary members being electrically connected distally of the insulation member to a common electrical supply conductor; and
   wherein the insulation member is formed with a least one wing, said at least one wing extending distally from the insulation member at a side of the tissue treatment electrode to project beyond the tissue treatment electrode.

2. An electrosurgial instrument as claimed in claim 1, wherein a plurality of separate, individual filaments constitute the filamentary members.

3. An electrosurgical instrument as claimed in claim 2, wherein the filaments each have a length lying within the range of from 0.5 mm to 5 mm.

4. An electrosurgical instrument as claimed in claim 2, wherein the filaments each have a diameter lying within the range of from 0.05 mm to 0.3 mm.

5. An electrosurgical instrument as claimed in claim 1, wherein a single coiled filament constitutes the filamentary members, the coils of the filament constituting the filamentary members.

6. An electrosurgical instrument as claimed in claim 1, wherein the filamentary members extend laterally through a cut-out formed in a side surface of the insulation member adjacent to the distal end thereof.

7. An electrosurgical instrument as claimed in claim 6, wherein the return electrode is formed with a hood-like extension which extends over the surface of the insulation member which is opposite the cut-out.

8. An electrosurgical instrument as claimed in claim 1, wherein the filamentary members are mounted within the insulation member in such a manner that they are axially movable relative to the insulation member between a first operating position, in which they extend partially from the insulation member, and a second operating position, in which they extend fully from the insulation member.

9. An electrosurgical instrument for the treatment of tissue in the presence of an electrically-conductive fluid medium, the instrument comprising;
   an instrument shaft, and an electrode assembly at one end of the shaft;
   the electrode assembly comprising a tissue treatment electrode and a return electrode which is electrically insulated from the tissue treatment electrode by means of an insulation member;
   the tissue treatment electrode being exposed at the distal end portion of the instrument, and the return electrode having a fluid contact surface spaced proximally from the exposed end of the tissue treatment electrode by the insulation member to an extent that the return electrode remains out of contact with tissue undergoing treatment by the tissue treatment electrode, so that electrical current flow between the tissue and the return electrode occurs only on a path through the conductive fluid medium;
   the exposed end of the tissue treatment electrode is constituted by a plurality of tissue treatment filament members made of an electrically-conductive material, the filamentary members being electrically connected to a common electrical supply conductor;
   wherein the lnsulation member is formed with a pair of diametrically-opposed wings at opposite sides of the tissue treatment electrode and extending distally from the insulation member at the sides of tie tissue treatment electrode to project beyond the tissue treatment electrode.

10. An electrosurgical instrument as claimed in claim 1, wherein the common electrical supply conductor is a central conductor, the insulation member surrounding the central conductor.

11. An electrosurgical instrument as claimed in claim 1, wherein the filamentary member are made of a precious metal such as platinum.

12. An electrosurgical instrument as claimed in claim 1, wherein the filamentary members are made of a platinum alloy such as platinum/iridium, platinum/tungsten or platinum/cobalt.

13. An electrosurgical instrument as claimed in claim 1, wherein the filamentary members are made of tungsten.

14. An electrosurgical instrument as claimed in claim 2, wherein the filaments each have a length lying within the range of from 5 mm to 10 mm.

15. An electrosurgical instrument as claimed in claim 14, wherein the filaments are made of stainless steel.

16. An electrosurgical instrument as claimed in claim 1, wherein the insulation member is made of a ceramic material.

17. An electrosurgical instrument as claimed in claim 1, wherein the insulation member is made of silicone rubber.

18. An electrosurgical instrument as recited in claim 1 wherein the filamentary members of the tissue treatment electrode are loops of a single coil having a central axis that is coincident with the instrument shaft's central axis.

19. The electrosurgical instrument as recited in claim 1 wherein the a least one wing extending distally from the insulation member prevents unnecessary exposure of adjacent body structures to the tissue treatment electrode.

20. An electrosurgical instrument for the treatment of tissue in the presence of an electrically-conductive fluid medium, the instrument comprising:

an instrument shaft, and an electrode assembly at one end of the shaft;

the electrode assembly comprising a tissue treatment electrode and a return electrode which is electrically insulated from the tissue treatment electrode by means of an insulation member;

the tissue treatment electrode being exposed at the distal end portion of the instrument, and the return electrode having an exposed fluid contact surface spaced proximally from the exposed end of the tissue treatment electrode by the insulation member to an extent that the return electrode remains out of contact with tissue undergoing treatment by the tissue treatment electrode, so that electrical current flow between the tissue and the return electrode occurs only on a path through the conductive fluid medium;

the exposed end of the tissue treatment electrode is constituted by a polarity of tissue treatment filamentary members made of an electrically-conductive material, the filamentary members being electrically connected to a common electrical supply conductor distally of the installation member; and the insulation member being formed with a least one extension, each extension protuding distally from the insulation member at a side of the tissue treatment electrode to project beyond the tissue treatment electrode.

21. An electrosurgical instrument as recited in claim 20 wherein the filamentary members of the tissue treatment electrode are loops of a single coil having a central axis that is coincident with the instrument shaft's central axis.

22. The electrosurgical instrument as recited in claim 20 wherein the at least one extension protruding distally from the insulation member prevents unnecessary exposure of adjacent body structures to the tissue treatment electrode.

23. A method of operating an electrosurgical apparatus having at least a tissue desiccation mode and a tissue vaporisation mode, the apparatus having a radio frequency generator coupled to an electrode assembly for the treatment of tissue in the presence of an electrically-conductive fluid medium, the electrode assembly comprising a tissue treatment electrode and a return electrode which is electrically insulated from the tissue treatment electrode by means of an insulation member, the tissue treatment electrode being exposed at a distal end portion of the assembly, the return electrode having an exposed fluid contact surface spaced proximally from the exposed end of the tissue treatment electrode by the insulation member, and the exposed end of the tissue treatment electrode being constituted by a plurality of tissue treatment filamentary members made of an electrically-conductive material the filamentary members being electrically connected distally of the insulation member to the radio frequency generator by a common electrical supply conductor, the method comprising the step of:

controlling the output power of the radio frequency generator to lie within a first output range for the tissue desiccation mode and to lie within a second range for the tissue vaporisation mode, the first output range being such that the power supplied to the electrode assembly maintains the conductive fluid adjacent to the tissue treatment electrode substantially at boiling point for tissue desiccation without creating a vapour pocket surrounding the tissue treatment electrode, and the second output range is such that the output power supplied to the electrode assembly for vaporisation of tissue is such as to maintain a vapour pocket surrounding the tissue treatment electrode.

24. A method as claimed in claim 23, wherein the tissue treatment electrode extends longitudinally from the extreme distal end of the instrument and is mounted within the insulation member in such a manner that it is axially movable relative to the insulation member between a first operating position, in which it is adjacent to the insulation member, and a second operating position, in which it is spaced from the distal end of the insulation member, and wherein the output power of the radio frequency generator is controlled to be in the first output range when the tissue treatment electrode is in its second operating position, and to be in the second output range when the tissue treatment electrode is in its first operating position.

25. A method as claimed in claim 23, wherein the first output range is from about 150 volts to 200 volts and the second output range is from about 250 volts to 600 volts, the voltages being peak voltages.

26. A method of operating an electrosurgical apparatus as claimed in claim 25, wherein the insulation member is formed with a least one wing extending distally from the insulation member at a side of the tissue treatment electrode to project beyond the tissue treatment electrode, and wherein the method further comprises protecting tissue adjacent to the application site using the distal projection of the insulating member.

27. A method of operating an electrosurgical apparatus having at least a tissue desiccation mode and a tissue vaporisation mode, the apparatus having a radio frequency generator coupled to an electrode assembly for the treatment of tissue in the presence of an electrically-conductive fluid medium, the electrode assembly comprising a tissue treatment electrode and a return electrode which is electrically insulated from the tissue treatment electrode by means of an insulation member, the tissue treatment electrode being exposed at a distal end portion of the assembly, the return electrode having a fluid contact surface spaced proximally from the exposed end of the tissue treatment electrode by the insulation member, and the exposed end of the tissue treatment electrode being constituted by a plurality of tissue treatment filamentary members made of an electrically-conductive material the film members being electrically connected to the radio frequency generator by a common electrical supply conductor the method comprising the step of:

controlling the output power of the radio frequency generator to lie within a first output range for the tissue desiccation mode and to lie within a second range for the tissue vaporisation mode, the first output range being such that the power supplied to the electrode assembly maintains the conductive fluid adjacent to the tissue treatment electrode substantially at boiling point for tissue desiccation without creating a vapour pocket surrounding the tissue treatment electrode, and the second output range is such that the output power supplied to the electrode assembly for vaporisation of tissue is such as to maintain a vapour pocket surrounding the tissue treatment electrode, wherein the insulation member is formed with a pair of diametrically opposed wings extending distally from the insulation member along the tissue treatment electrode's sides to project beyond the tissue treatment electrode, and wherein the method further comprises using the diametrically opposed wings to protect tissue adjacent to the application site and to assist in engaging the tissue treatment electrode with laminar tissue structures.

28. An electrosurgical tissue desiccation method comprising the steps of:

providing an electrosurgical apparatus comprising a radio frequency generator coupled to an electrode assembly comprising a tissue treatment electrode and a return electrode having an exposed fluid contact surface spaced proximally from the treatment electrode by an insulation member, the tissue treatment electode being exposed at a distal end portion of the assembly and being constituted by a plurality of tissue treatment filamentary members made of an electrically-conductive material, the filamentay members being electrically connected to the radio frequency generator distally of the insulation member by a common electrical conductor;

introducing the electrode assembly into a selected operation site with the tissue treatment electrode contacting the tissue to be treated, and with the tissue and the electrode assembly immersed in a conductive liquid;

activating the generator; and controlling the radio frequency power supplied to the electrode assembly by the generator to maintain the conductive liquid adjacent to the tissue treatment electrode substantially at its boiling point without creating a vapour pocket surrounding the tissue treatment electrode.

29. A method as claimed in claim 28, wherein the return electrode is spaced proximally with respect with to the tissue treatment electrode, and wherein the electrode assembly is introduced into the selected operation site such that the tissue treatment electrode is in contact with the tissue to be treated, and the return electrode is immersed in the conductive liquid, the electrode assembly being manipulated to cause heating and desiccation of the tissue in a required region adjacent to the tissue treatment electrode.

30. A method as claimed in claim 29, wherein the electrode assembly is manipulated by moving the tissue treatment electrode across the surface of the tissue to be treated in a side-to-side "painting" technique.

31. An electrosurgical method comprising the steps of:

providing an electrosurgical apparatus comprising a radio frequency generator coupled to an electrode assembly comprising a tissue treatment electrode and a return electrode separated by an insulation member, The tissue treatment electrode being exposed at a distal end portion of the assembly, the return electrode having a fluid contact surface spaced proximally from the treatment electrode, and being constituted by a plurality of tissue treatment filamentary members made of an electrically-conductive material, the filamentary members being electrically connected to the radio frequency generator distally of the insulation member by a common electrical supply conductor;

introducing the electrode assembly into a selected operation site with the tissue treatment electrode adjacent to the tissue to be treated, and with the tissue and the tissue electrode assembly immersed in a conductive liquid;

activating the generator; and applying sufficient radio frequency power to the electrode assembly to vaporise the conductive liquid surrounding the tissue treatment electrode to maintain a vapour pocket surrounding the tissue treatment electrode.

32. A method as claimed in claim 31, further comprising the step of controlling the radio frequency power to prevent the tissue contact electrode overheating.

33. A method as claimed in claim 31, wherein the return electrode is spaced proximally with respect to the tissue treatment electrode, and wherein the electrode assembly is introduced into the selected operation site such that the tissue treatment electrode is positioned at least adjacent to the tissue to be treated, with the vapour pocket in contact with the tissue, and with the return electrode immersed in the conductive liquid, the electrode structure being manipulated to achieve at least vaporisation of the tissue.

34. A method as claimed in claim 31, for debulking a tumour having a portion projecting into an internal body cavity, the method further comprising the steps of removing the projecting portion, and then removing the portion embedded within the body tissue without vaporising surrounding body tissue.

35. An electrosurgical method as claimed in claim 31, wherein the insulation member is formed with a least one wing extending distally from the insulation member at a side of the tissue treatment electrode to project beyond the tissue treatment electrode, and wherein the method further comprises protecting tissue adjacent to the application site using the distal projection of the insulating member.

36. An electrosurgical method comprising the steps of:

providing an electrosurgical apparatus comprising a radio frequency generator coupled to an electrode assembly comprising a tissue treatment electrode and a return electrode, the tissue treatment electrode being exposed at a distal end portion of the assembly and being constituted by a plurality of tissue treatment filamentary members made of an electrically-conductive material, the filamentary members being electrically connected to the radio frequency generator by a common electrical supply conductor;

introducing the electrode assembly into a selected operation site with the tissue treatment electrode adjacent to the tissue to be treated, and with the tissue and the tissue electrode assembly immersed in a conductive liquid;

activating the generator; and applying sufficient radio frequency power to the electrode assembly to vaporise the conductive liquid surrounding the tissue treatment electrode to maintain a vapour pocket surrounding the tissue treatment electrode wherein the insulation member is foxed with a pair of diametrically opposed wings extending distally from the insulation member at sides of the tissue treatment electrode to project beyond the tissue treatment electrode, and wherein the method further comprises using the diametrically opposed wings to protect tissue adjacent to the application site and to assist in engaging the tissue treatment electrode with laminar tissue structures.

37. A method of desiccating tissue using a bipolar electrode assembly, the bipolar electrode assembly including an active electrode and an exposed return electrode insulated from the active electrode by an insulation member, the active electrode having a plurality of tissue treatment filamentary members connected at a common electrical point distally of the insulation member, said filamentary members each having a tip and a proximal portion, the method comprising the steps of:

(a) introducing the electrode assembly into a selected operation site;

(b) surrounding the electrode assembly with a conductive fluid;

(c) applying sufficient radio frequency output power to the electrode assembly to raise the temperature of the conductive fluid adjacent to the active electrode without creating a vapour pocket surrounding the active electrode;

(d) contacting one or more filament tips of the active electrode to the tissue while maintaining the return electrode out of contact with the tissue.

38. A method as claimed in claim 37, wherein step (d) includes maintaining the proximal portions of the filamentary members out of contact with the tissue.

39. A method as claimed in claim 37, wherein step (d) includes the further step of:

(e) moving the active electrode across the surface of the tissue.

40. A method as claimed in claim 39, wherein step (d) includes moving the electrode across the tissue surface in a side-to-side motion.

41. A method as claimed in claim 37, wherein step (c) includes maintaining the temperature of the conductive fluid adjacent to the active electrode substantially at the boiling point of the conductive fluid.

42. A method as claimed in claim 37, wherein the conductive fluid is a saline solution.

43. A method of vaporising tissue using a bipolar electrode assembly, the bipolar electrode assembly including an active electrode and an exposed return electrode separated from the active electrode by an insulation member, the active electrode having a plurality of tissue treatment filamentary members connected at a common electrical point distally of the insulation member, said filamentary members each having a tip and a proximal portion, the method comprising the steps of:

(a) introducing the electrode assembly into a selected operation site;

(b) surrounding the electrode assembly with a conductive fluid;

(c) applying sufficient radio frequency output power to the electrode assembly to vaporise the conductive fluid adjacent to the active electrode to create a vapour pocket surrounding the active electrode;

(d) positioning one or more filament tips of the active electrode adjacent to the tissue with the vapour pocket in contact with the tissue while maintaining the return electrode out of contact with the tissue.

44. A method as claimed in claim 43, wherein step (d) includes maintaining the proximal portions of the filamentary members out of contact with the tissue.

45. A method as claimed in claims 44, wherein step (d) includes the further step of:

(e) moving the active electrode over the surface of the tissue.

46. A method as claimed in claim 45, wherein step (e) includes moving the electrode over the tissue surface in a side-to-side motion.

47. A method as claimed in claim 43, wherein the conductive fluid is a saline solution.

48. An electrosurgical method comprising the steps of:

providing an electrosurgical apparatus comprising a radio frequency generator coupled to an electrode assembly comprising a tissue treatment electrode and a return electrode insulated from the treatment electrode by an insulation member, the tissue treatment electrode being exposed at the distal end portion of the assembly and being constituted by a plurality of tissue treatment filamentary members made of an electrically-conductive material, the return electrode having an exposed fluid contact surface spaced proximally of the active electrode, the filamentary members being electrically connected to the radio frequency generator by a common electrical supply conductor distally of the insulation member;

introducing the electrode assembly into a selected operation site with the tissue treatment electrode adjacent to the tissue to be treated, and with the tissue and the tissue electode assembly immersed in a conductive liquid;

activating the generator; and applying sufficient radio frequency power to the electrode assembly to vaporize the conductive liquid surrounding the tissue treatment electrode to maintain a vapour pocket surrounding the tissue treatment electrode;

wherein the return electrode is spaced proximally with respect to the tissue treatment electrode, and wherein the electrode assembly is introduced into the selected operation site such that the tissue treatment electrode is positioned at least adjacent to the tissue to be treated, with the vapour pocket in contact with the tissue, and with the return electrode imbersed in the conductive liquid, the electrode structure being manipulated to achieve at least vaporization of the tissue; and fixer comprising the step of creating a plurality of holes of predetermined depth in tissue to be removed by drilling into the tissue.

* * * * *